(12) United States Patent
Raniere

(10) Patent No.: US 9,393,351 B2
(45) Date of Patent: Jul. 19, 2016

(54) CLONED BIOLOGICAL MATERIAL MEDICAL DEVICE AND METHOD THEREOF

(71) Applicant: First Principles, Inc., Albany, NY (US)

(72) Inventor: Keith A Raniere, Clifton Park, NY (US)

(73) Assignee: FIRST PRINCIPLES, INC., Albany, NY (US)

( * ) Notice: Subject to any disclaimer, the term of this patent is extended or adjusted under 35 U.S.C. 154(b) by 96 days.

(21) Appl. No.: 14/034,977

(22) Filed: Sep. 24, 2013

(65) Prior Publication Data

US 2014/0023687 A1    Jan. 23, 2014

Related U.S. Application Data

(62) Division of application No. 13/044,591, filed on Mar. 10, 2011, now Pat. No. 8,597,948.

(51) Int. Cl.

| | |
|---|---|
| *C12N 5/00* | (2006.01) |
| *A61B 5/04* | (2006.01) |
| *A61L 29/16* | (2006.01) |
| *A61L 27/36* | (2006.01) |
| *A61L 27/38* | (2006.01) |
| *A61L 29/00* | (2006.01) |
| *A61M 1/14* | (2006.01) |
| *A61K 35/16* | (2015.01) |
| *A61K 35/32* | (2015.01) |
| *A61K 35/34* | (2015.01) |
| *A61K 35/35* | (2015.01) |
| *A61K 35/36* | (2015.01) |
| *A61F 2/24* | (2006.01) |
| *A61N 1/36* | (2006.01) |

(52) U.S. Cl.
CPC .............. *A61L 29/16* (2013.01); *A61F 2/2442* (2013.01); *A61K 35/16* (2013.01); *A61K 35/32* (2013.01); *A61K 35/34* (2013.01); *A61K 35/35* (2013.01); *A61K 35/36* (2013.01); *A61L 27/3683* (2013.01); *A61L 27/3804* (2013.01); *A61L 29/005* (2013.01); *A61M 1/14* (2013.01); *A61N 1/36* (2013.01)

(58) Field of Classification Search
CPC ..................... C12N 5/00; A61B 5/04
See application file for complete search history.

(56) References Cited

U.S. PATENT DOCUMENTS

| | | |
|---|---|---|
| 4,485,096 A | 11/1984 | Bell |
| 4,963,489 A | 10/1990 | Naughton et al. |
| 5,032,508 A | 7/1991 | Naughton et al. |
| 5,100,783 A | 3/1992 | Dean, Jr. et al. |
| 5,650,389 A | 7/1997 | Krumdieck et al. |
| 5,811,535 A | 9/1998 | Adamou et al. |
| 5,863,531 A | 1/1999 | Naughton et al. |
| 6,472,181 B1 | 10/2002 | Mineau-Hanschke |
| 6,547,719 B1 * | 4/2003 | Atala et al. ............... 600/40 |
| 6,900,055 B1 | 5/2005 | Fuller et al. |
| 2003/0059463 A1 | 3/2003 | Lahtinen |
| 2004/0191900 A1 | 9/2004 | Mizuno et al. |
| 2005/0042254 A1 | 2/2005 | Freyman et al. |
| 2005/0181505 A1 * | 8/2005 | Amir et al. ............... 435/396 |
| 2005/0226853 A1 | 10/2005 | Conrad et al. |
| 2006/0199265 A1 | 9/2006 | Wolf et al. |
| 2007/0276507 A1 * | 11/2007 | Bertram et al. ............ 623/23.65 |
| 2009/0291415 A1 * | 11/2009 | Binderman et al. ....... 433/200.1 |
| 2012/0197392 A1 | 8/2012 | DuMontelle et al. |
| 2012/0231036 A1 | 9/2012 | Raniere |

FOREIGN PATENT DOCUMENTS

WO    WO90/09582    *    9/1997    ............... A61F 2/02

OTHER PUBLICATIONS

Office Action (mail date Mar. 22, 2013) for U.S. Appl. No. 13/044,591 filed Mar. 10, 2011.
Notice of Allowance (mail date Jul. 31, 2013) for U.S. Appl. No. 13/044,591 filed Mar. 10, 2011.

* cited by examiner

*Primary Examiner* — Karen Cochrane Carlson
*Assistant Examiner* — Natalie Moss
(74) *Attorney, Agent, or Firm* — Schmeiser, Olsen & Watts, LLP

(57) ABSTRACT

A medical device, said medical device, comprises: a first component having a non-biological material; a second component having a cloned biological material, said second component being attached to said first component, wherein said first component and said second component are operatively associated in a non-living medical device for at least one of treatment, diagnosis, cure, mitigation and prevention of disease, injury, handicap or condition in a living organism. In another aspect, a method comprises: preparing a cloned biological material from a tissue or an organ; attaching said biological material to a medical device; interfacing said biological material with the non-biological material; providing treatment, diagnosis, cure, mitigation and prevention of disease, injury, handicap or condition in a living organism.

19 Claims, 22 Drawing Sheets

CLONED BIOLOGICAL MATERIAL MEDICAL DEVICE AND METHOD THEREOF

CROSS-REFERENCE TO RELATED APPLICATION

This application is a divisional application of U.S. application Ser. No. 13/044,591, filed Mar. 10, 2011, and entitled, A Cloned Biological Material Medical Device and Method Thereof."

BACKGROUND

1. Field of Disclosure

The present invention relates generally to medical devices and method for reducing or preventing immune reactions and improving circuitry.

2. Related Art

The tissue-equivalents of Bell, U.S. Pat. No. 4,485,096, are living prostheses comprising contracted hydrated lattices of tissue and cells, including cartilage, fibroblasts, keratinocytes, bone cells, pancreatic cells and heart muscle cells. The tissue-equivalents are formed as sheets, tubes and other shapes in a mold. Naughton et al., U.S. Pat. No. 5,863,531 is an in vitro preparation of tubular tissue structures by stromal cell culture on a three-dimensional framework. Stromal cells are grown on a three-dimensional framework and formed into three-dimensional living stromal tissue of various shapes, including tubular structures, flat structures and rope structures. The method for the inhibition of compliment activation, set forth in Krumdieck et al., U.S. Pat. No. 5,650,389 comprises coating biomaterial with proteogylcan to suppress or inhibit C 1 complex biological activity. The proteogylcan inhibit the complement response of a human or an animal to the foreign materials such as microorganisms, pathogens or biomaterials. A disadvantage of prior inventions is that the cellular material or tissue is not used on a medical device or as part of machine. There exists a need for a medical device comprising cloned biological material operatively associated to a non-biological material in a non-living medical device for treatment, diagnosis, cure, litigation and prevention of disease, injury, handicap or condition in a living organism.

SUMMARY

A medical device, said medical device, comprising: a first component having a non-biological material; a second component having a cloned biological material, said second component being attached to said first component, wherein said first component and said second component are operatively associated in a non-living medical device for at least one of treatment, diagnosis, cure, mitigation and prevention of disease, injury, handicap or condition in a living organism.

In another aspect, a method comprising: preparing a cloned biological material from a tissue or an organ; attaching said biological material to a medical device; interfacing said biological material with the non-biological material; providing treatment, diagnosis, cure, mitigation and prevention of disease, injury, handicap or condition in a living organism.

DETAILED DESCRIPTION

The present invention will be described in association with references to drawings; however, various implementations of the present invention will be apparent to those skilled in the art.

Figure 1:
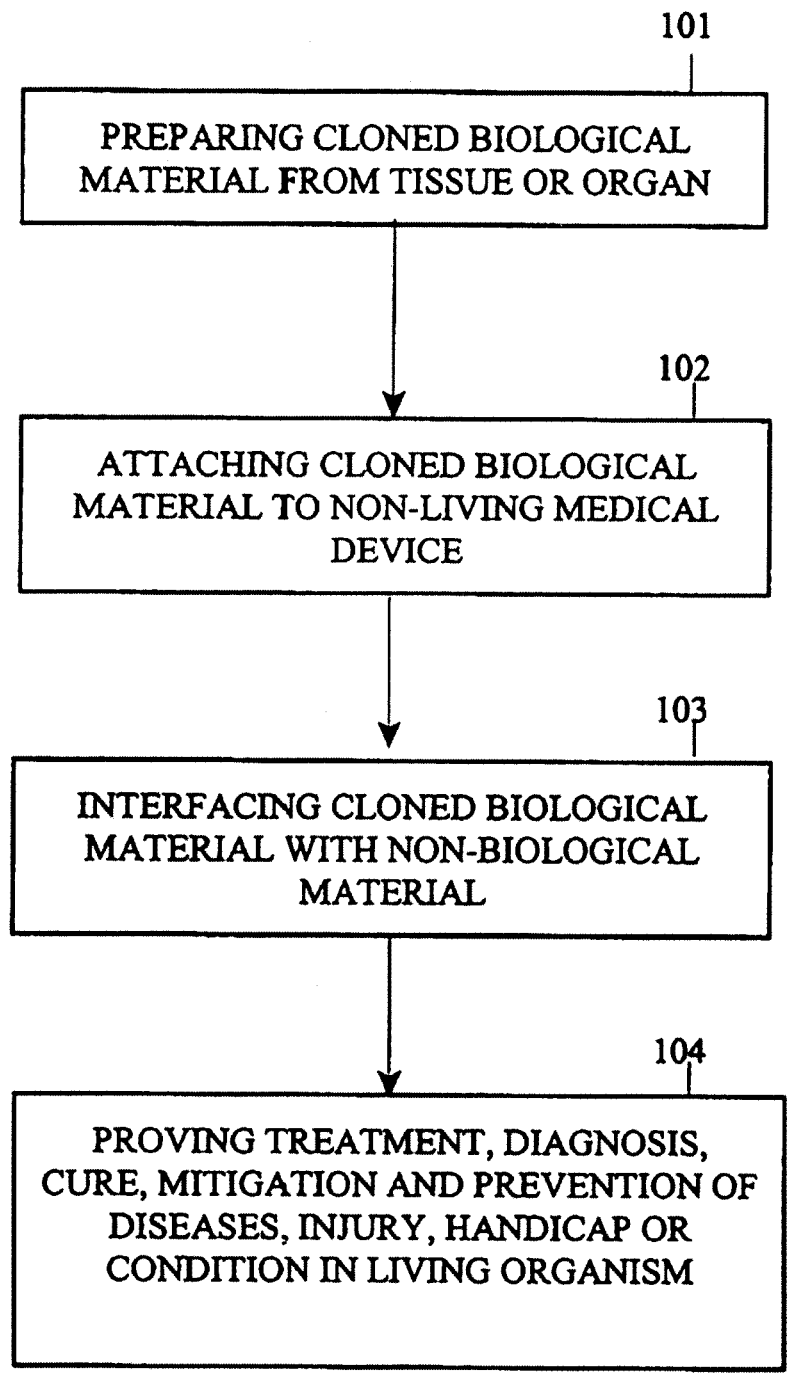
FIG. 1 illustrates method comprising: preparing a cloned biological material from a tissue or an organ, attaching the biological material to a medical device, interfacing the biological material with the non-biological material for treatment, diagnosis, cure, mitigation and prevention of disease, injury, handicap or condition in a living organism.

FIG. 1 illustrates a method comprising: preparing a cloned biological material from a tissue or an organ in step 101, attaching a biological material to a medical device in step 102, interfacing the biological material with the non-biological material in step 103 and providing treatment, diagnosis, cure, mitigation and prevention of disease, injury, handicap or condition in a living organism in step 104.

In one aspect, the method of preparing a cloned biological material (i.e., a shaped tissue structure or a shaped organ structure) from a tissue or an organ includes removing a portion of the tissue or the organ from an individual; isolating a cellular material from the portion of the tissue or the organ; dissociating the cellular material into a cell suspension using cell separation to obtain desired cells; and growing the desired cells on a shaped matrix to form the cloned biological material (i.e., shaped tissue structure or shaped organ structure). The method of removing a portion of a tissue or an organ from an individual may include excising a portion of the tissue or the organ. The method of isolating the cellular material from a portion of the tissue or the organ may include disaggregating cellular material from the tissue with a digestive enzyme (i.e., trysin, chymotrysin, collagenase, elastase, hydraluronidase, DNase, pronase, disease) and/or treating the tissue or organ with a chelating agent. The method of dissociating the cellular material into a cell suspension using cell separation to obtain desired cells may include cell separation by negative separation, filtration, centrifugation, electrophoresis, unit gravity separation and/or cloning and cell selection.

Figure 2A:
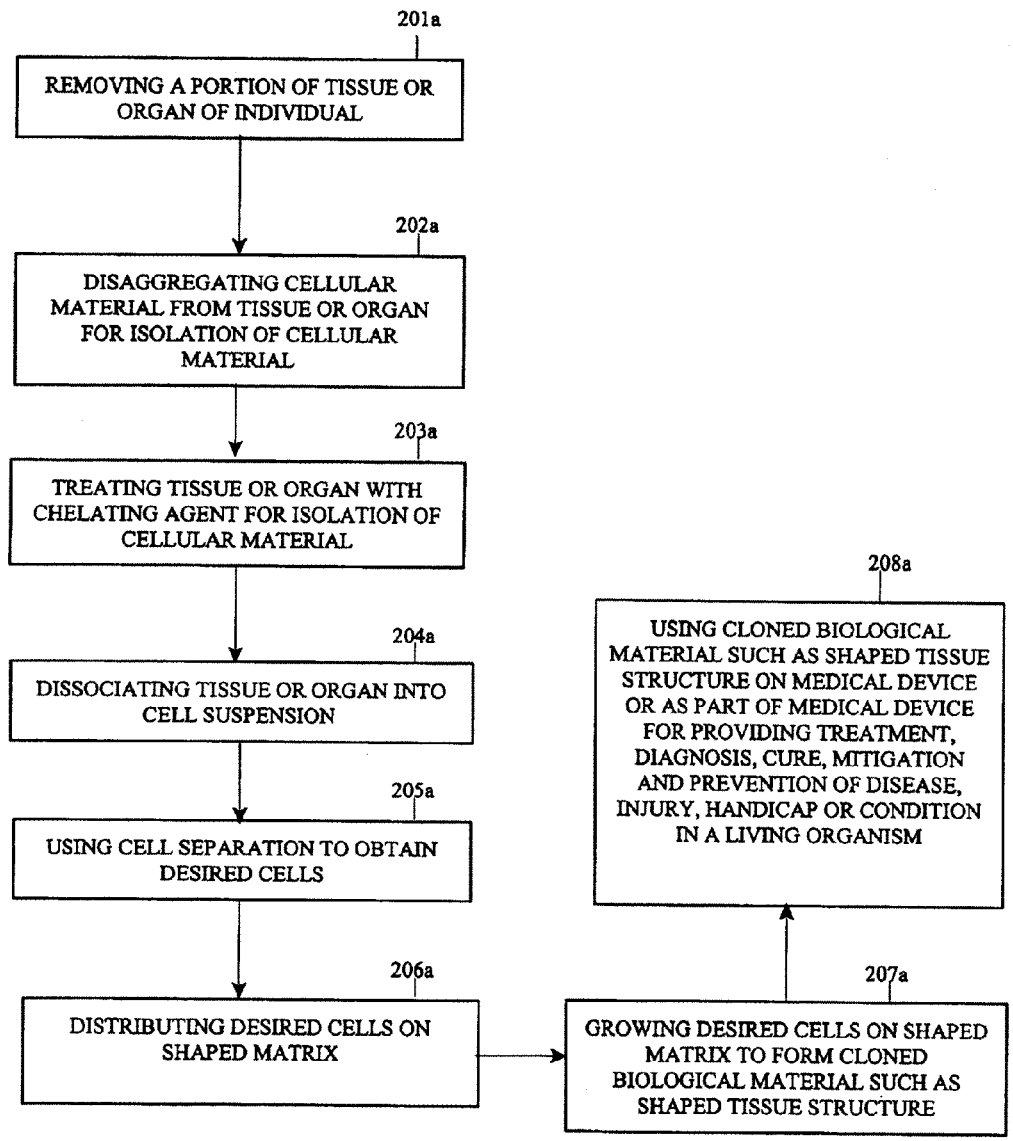
FIG. 2A illustrates a method of preparing a cloned biological material such as a shaped tissue structure from a tissue or organ of an individual for use on a non-living medical device or as part of a non-living medical device for treatment, diagnosis, cure, mitigation and prevention of disease, injury, handicap or condition in a living organism.

For example, FIG. 2A illustrates a method of preparing a cloned biological material (i.e., a shaped tissue structure or a shaped organ structure) from a tissue or organ of an individual for use on a medical device or as part of the medical device for treatment, diagnosis, cure, mitigation and prevention of disease, injury, handicap or condition in a living organism. Cellular material may be removed from the tissue or organ of an individual in step 201a. The tissue or organ may be disaggregated to isolate cellular material in step 202a of FIG. 2. The tissue or organ may also be treated with a chelating agent for isolation of cellular material in step 203a. The tissue or organ is dissociated into a cell suspension in step 204a. In step 205a, cell separation methods (i.e., negative separation, filtration, centrifugation, electrophoresis, unit gravity separation and cloning and cell selection) may be used to obtain desired cells from the cell suspension. The desired cells are distributed on a shaped matrix in step 206a. The cells are grown on the shaped matrix (e.g., a tubular matrix, thread-like matrix, twisted rope matrix, flat matrix, sheet matrix, spherical matrix, rod matrix, cubical matrix and/or other shaped matrix) to form a cloned biological material (i.e., a shaped tissue structure or a shaped organ structure) in step 207a. According to step 208a, the shaped tissue structure may be used on a non-living medical device or as part of a non-living medical device for providing treatment, diagnosis, cure, mitigation and prevention of disease, injury, handicap or condition in a living organism.

An increased risk of thrombosis, clotting and hyperplasia may result where medical devices, comprise artificial materials that comes in contact with the body. Medical devices, comprising autologous material, have been used to prevent or reduce the risk of thrombosis, clotting and hyperplasia. The tissue structures or organ structures of the present invention prevent the compliment activation of blood such as the creation of microemboli, which occurs from contact with artificial material of a medical device.

Figure 2B:
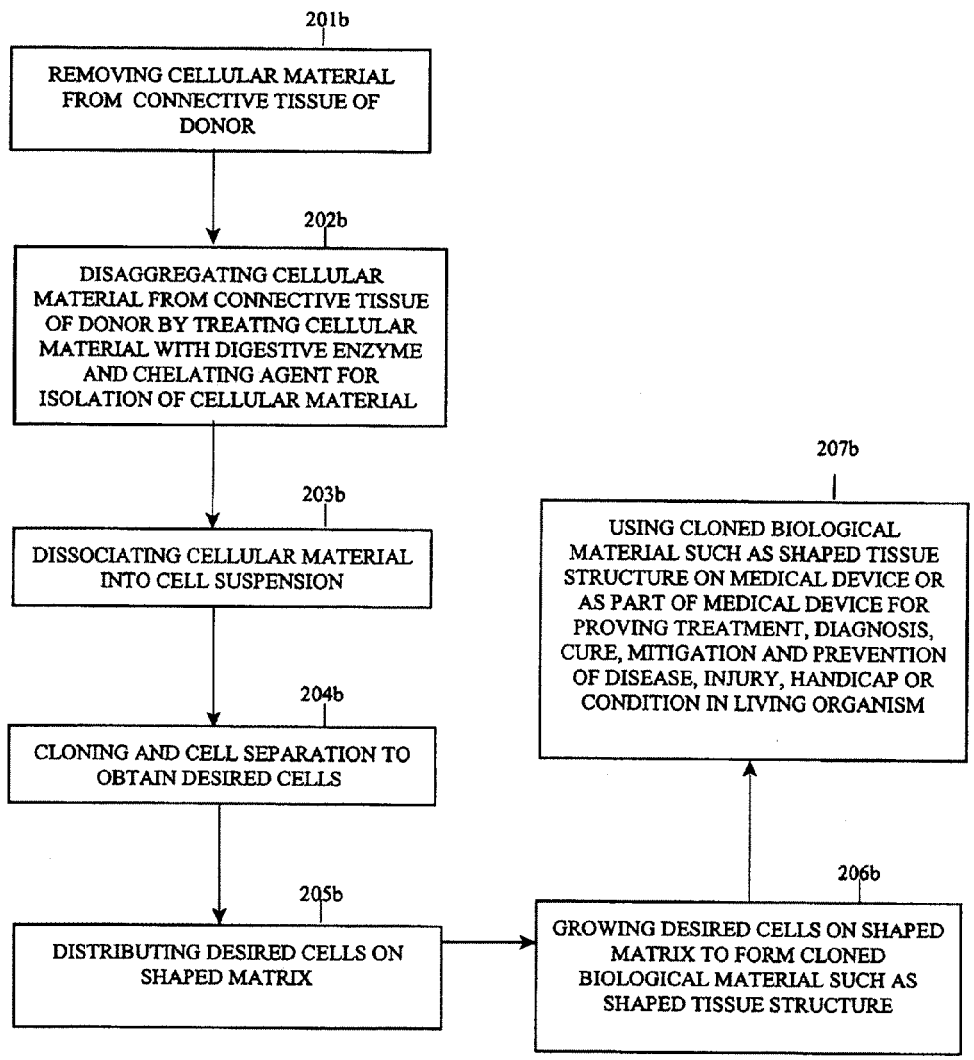
FIG. 2B illustrates a method of preparing a cloned biological material such as a shaped tissue structure from a connective tissue of a donor for use on a medical device or as part of a non-living medical device for treatment, diagnosis, cure, mitigation and prevention of disease, injury, handicap or condition in a living organism.

In another aspect of the present invention, the method of preparing a cloned biological material (i.e., a shaped tissue structure or a shaped organ structure) from a tissue or an organ includes removing a portion of a tissue or an organ from a donor; isolating a cellular material from the portion of the tissue or the organ; dissociating the cellular material into a cell suspension using cell separation to obtain desired cells; and growing the desired cells on a shaped matrix to form the cloned biological material (i.e., shaped tissue structure or shaped organ structure). For example, FIG. 2B illustrates a method of preparing a cloned biological material (i.e., shaped tissue structure) from a connective tissue of a donor. Cellular material may be removed from the connective tissue of a donor in step 201b of FIG. B. The cellular material is isolated from the connective tissue of the donor in step 202b. The cellular material may be disaggregated from the connective tissue of the donor with a digestive enzyme (i.e., trysin, chymotrysin, collagenase, elastase, hydraluronidase, DNase, pronase, dispase) and/or treating the tissue or organ with a chelating agent in step 202b. After the cellular material is isolated from the connective tissue of the donor in step 201 b and the cellular material is dissociated into a cell suspension in step 203b, the desired cells (i.e., pericytes, adipoctyes, macrophages, monocytes, plasma cells, mast cells and endothelial cells) may be obtained using cell separation methods (i.e., negative separation, filtration, centrifugation, electrophoresis, unit gravity separation and cloning and cell selection) in step 204b. The desired cells are distributed on a matrix (e.g., a tubular matrix, thread-like matrix, twisted rope matrix, flat matrix, sheet matrix, spherical matrix, rod matrix, cubical matrix and/or other shaped matrix) in step 205b. According to steps 206b and 207b, the desired cells are grown on the shaped matrix for use on a non-living medical device or as part of a non-living medical device for providing treatment, diagnosis, cure, mitigation and prevention of disease, injury, handicap or condition in a living organism.

The method of preparing a cloned biological material (i.e., a shaped tissue structure or a shaped organ structure) from a tissue or an organ may further include genetically modifying cells to express or inactivate the expression of proteins, enzymes, or factors for prevention or reduction of thrombosis, hyperplasia, inflammation, occlusion, and immunological reactions. The cells may be genetically modified (e.g., using ribozymes, vectors, endogenous cellular gene activation or repression, small molecule regulation, over expression of cDNA clones, antisense, gene knock outs etc.) to alter gene expression. The vectors, comprising DNA segments may be introduced to cells via transfer methods such as transfection, transduction, calcium phosphate-mediated transformation, microinjection, electroporation or osmotic shock. Cells may be genetically modified to activate enzymes or factors or genetically modified to inactivate the expression of enzymes or factors for prevention or reduction of thrombosis, hyperplasia, inflammation, occlusion, and other immunological reactions. For instance, the cells may be genetically modified to express anti-inflammatory peptides, proteins, or factors such as anti-GM-CSF, anti-TNF, anti-IL-1, anti-IL-2. Cells may be genetically modified to express anticoagulation gene products, which improve platelet aggregation and prevent or decrease blood coagulation and thromboembolism. The cells may be genetically modified for expression of enzymes, including streptokinase, tissue plasminogen activator and urokinase for clot reduction. The cells may be genetically modified to prevent or reduce hyperplasia by blocking expression of antisense oligodeoxynucleotide. The cells may be genetically modified to inactivate gene expression via partial gene deletion or complete gene deletion.

The cells may be genetically modified to inactivate gene expression by preventing production of messenger RNA (mRNA). Proteins are a product of gene expression. A promoter is located upstream of genes on the DNA. RNA polymerase binds to the promoter of the DNA. As RNA polymerase travels down one strand of the DNA during transcription, RNA polymerase reads the nucleotide base sequence of the DNA. RNA polymerase makes a complementary strand of mRNA. A repressor protein, located downstream of the promoter site, can be used to physically block RNA polymerase from traveling down the strand of the DNA and producing mRNA during transcription. Ribosomes translate mRNA into proteins during translation, which occurs after transcription. Since a repressor protein prevents production of the mRNA during transcription, a particular protein may not be produced during translation.

Figure 2C:
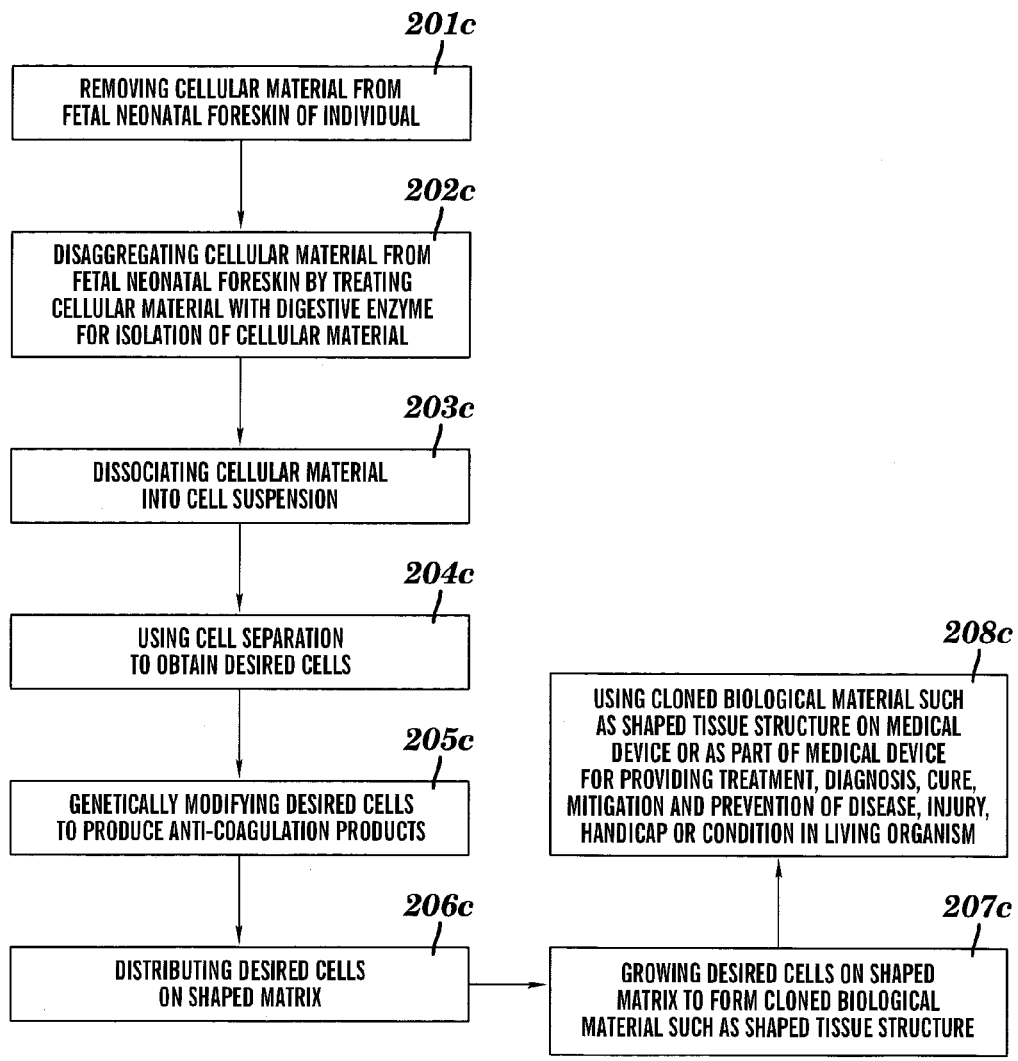
FIG. 2C provides an example of a method of preparing a cloned biological material such as a shaped tissue structure or a shaped organ structure from a tissue or an organ, further including genetically modifying cells to express or inactivate the expression of a protein, an enzyme, or a factor for treatment, diagnosis, cure, mitigation and prevention of disease, injury, handicap or condition in a living organism.

FIG. 2C provides an example of a method of preparing a cloned biological material (i.e., a shaped tissue structure or a shaped organ structure) from a tissue or an organ, further including genetically modifying cells to express or inactivate the expression of a protein, an enzyme, or a factor for prevention or reduction of thrombosis, hyperplasia, inflammation, occlusion, and immunological reactions. In step 201c of FIG. 2C, cellular material may be removed from fetal neonatal foreskin. The cellular material may be isolated from the fetal neonatal foreskin in step 202c. The cellular material may be treated with digestive enzymes to disaggregate the cellular material from the fetal neonatal foreskin in step 202c. The cellular material is dissociated into a cell suspension in step 203c and cell separation is used to obtain desired cells in step 204c. Optionally, the cells may be genetically modified to produce anti-coagulation products in step 205c. The desired cells are inoculated and grown on a shaped matrix in steps 206c and 207c. As the desired cells grow on the shaped matrix, a shape tissue structure is formed in step 207c. The shaped tissue structure is used on a non-living medical device or as part of a non-living medical device for proving treatment, diagnosis, cure, mitigation and prevention of disease, injury, handicap or condition in a living organism in step 208c.

Figure 3:
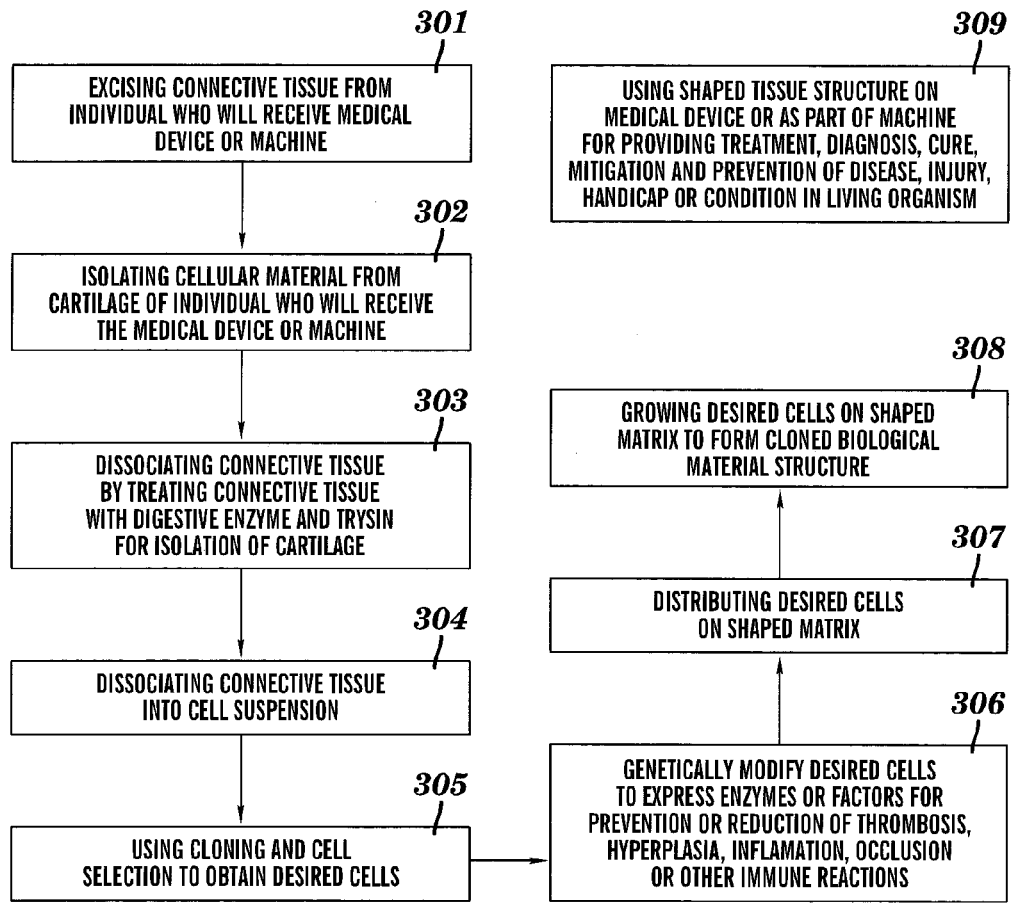
FIG. 3 provides an example of a method of dissociating the cellular material into a cell suspension using cell separation to obtain desired cells, wherein cell separation is cloning and cell selection.

FIG. 3 provides an example of a method of dissociating the cellular material into a cell suspension using cell separation to obtain desired cells, wherein cell separation is cloning and cell selection. In accordance with step 301 of FIG. 3, connective tissue such as cartilage (i.e., articular cartilage, auricular cartilage, costal cartilage, elastic cartilage, fibrous cartilage, hyaline cartilage, meniscal cartilage and yellow cartilage) may be excised from an individual, who will receive a non-living medical device or a part of a non-living medical device. The cellular material may be isolated from cartilage in step 302. Articular chronodrocytes may be isolated from the articular cartilage, a connective tissue comprising chondrocytes in the extracellular matrix. Articular cartilage is located on the articular surfaces of the bone in an individual. The cartilage may be disaggregated and treated with digestive enzymes (i.e., trysin, chymotrysin, collagenase, elastase, hydraluronidase, DNase, pronase, disease) and/or chelating agents such as trysin in step 304. The cellular material is dissociated in a cell suspension in step 304. Then, the desired cells (i.e., articular chronodrocytes) are obtained from the dissociated piece of cartilage using cloning and cell election in step 305. The desired cells may be genetically modified to express enzymes or factors for prevention or reduction of thrombosis, hyperplasia, inflammation, occlusion or other immune reactions in step 306. The desired cells are distributed as a suspension on a shaped matrix in step 307. The shapes of the matrix may be tubular, thread-like, twisted, flat, spherical, rod-like or cubical. Those of ordinary skill in the art will know how to modify the shape of matrix without departing from the spirit of the invention. The desired cells are grown on the shaped matrix to form a shaped tissue structure in step 308. The cloned biological material (i.e., shaped tissue structure) is used on a non-living medical device or as part of the non-living medical device for proving treatment, diagnosis, cure, mitigation and prevention of disease, injury, handicap or condition in a living organism in step 309.

The shaped matrix may comprise porous material, non-porous material, biodegradable material (e.g., polyglycolic acid, collagen, polyorthoesters, polycaprolactones, collagen sponge, woven collagen, gelatin, polylactic acid, polyglycolic acid) and/or non-biodegradable material (e.g., polyamides, polyesters, polyesteramide, polystrene, fluorinated ethylene propylene, polypropylene, polyacrylates, polyvinyl, polycarbonate, polytetrafluoroethylene, polyethylene, polyethylene terapthalate, silicone, silicone rubber, polysulfone, thermanox, polyurethane, polyacrylics, polyhydroxymethyacrylates, nitrocellulose, cotton).

Figure 4:
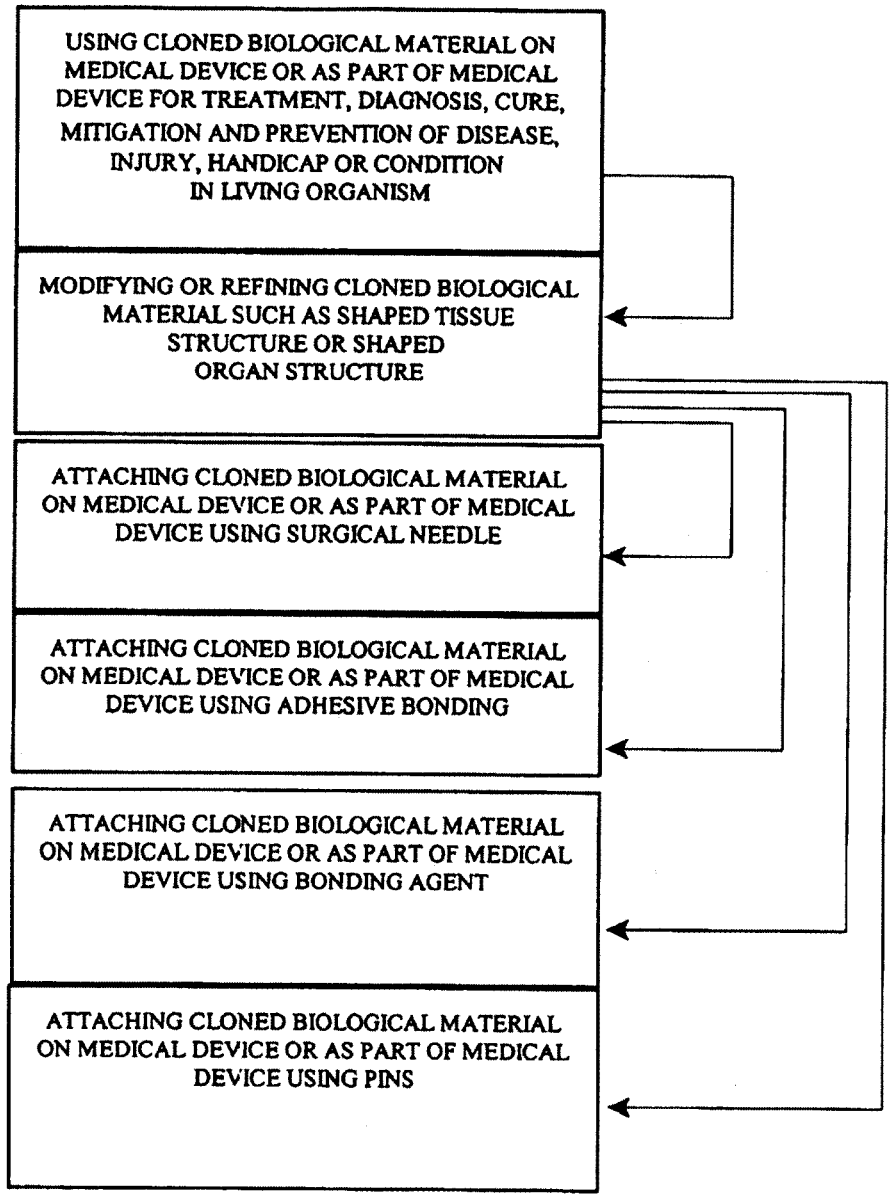
FIG. 4 illustrates a method of using a cloned biological material such as a shaped tissue structure or shaped organ structure on a medical device or as part of a medical device, including modifying or refining the shaped tissue structure or shaped organ structure.

The method of using a cloned biological material (i.e., a shaped tissue structure or shaped organ structure) on a non-living medical device or as part of a non-living medical device may include modifying or refining the cloned biological material (i.e., shaped tissue structure or shaped organ structure). Once the cells derived from tissue or organs are inoculated and grown on the matrix, then the cell may be grown to form cloned biological materials of various shapes (i.e., shaped tissue structures or shaped organ structures of various shapes, including tubular structures, thread-like structures, twisted rope structures, flat structures, sheet structures, spherical structures, rod structures, cubical structures, and/or other shaped structures.) For example, blood vessels may be constructed from tubular structures. The cloned biological materials (i.e., shaped tissue structures or shaped organ structures) may also be of various thicknesses. The dimensions of the cloned biological material (i.e., shaped tissue structure or shaped organ structure) may be modified or refined using medical instruments, including but not limited to lasers, surgical scissors and scalpels. FIG. 4 illustrates a method of using a cloned biological material (i.e., a shaped tissue structure or a shaped organ structure) on a non-living medical device or as part of a non-living medical device, including modifying or refining the shaped tissue structure or shaped organ structure.

Figure 5:
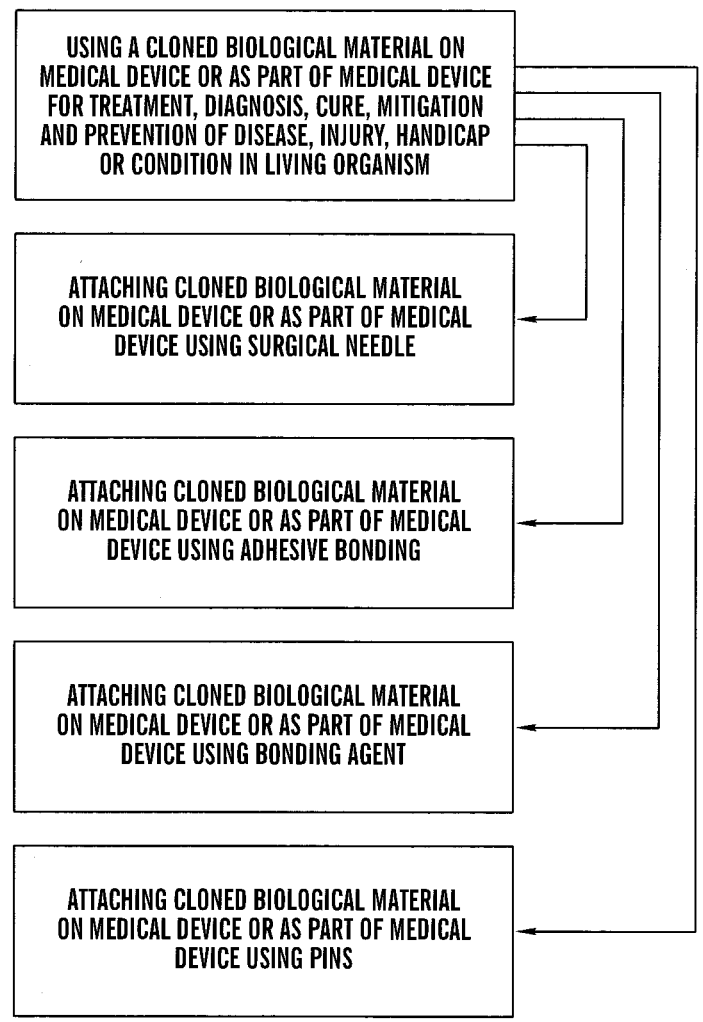
FIG. 5 illustrates a method of using a cloned biological material such as a shaped tissue structure or shaped organ structure on a medical device or as part of a medical device, including the attachment of the cloned biological material on a medical device or as a part of the medical device.

The method of using a cloned biological material (i.e., a shaped tissue structure or a shaped organ structure) on a non-living medical device or as a part of the non-living medical device may include attaching the cloned biological material on the non-living medical device or as a part of the non-living medical device. FIG. 5 illustrates a method of using a cloned biological material (i.e., a shaped tissue structure or shaped organ structure) on a non-living medical device or as part of a non-living medical device may include attaching the shaped cloned biological material on a non-living medical device or as a part of the non-living medical device. The cloned biological material (i.e., shaped tissue structure or shaped organ structure) is attached on a non-living medical device or attached as a part of the non-living medical device via attachment methods known to those skilled in the art (i.e., surgical needle, adhesive bonding, bonding agent, pins).

The cloned biological materials (i.e., shaped tissue structures or shaped organ structures) may be used on a non-living medical devices, including, but are not limited to medical machines, pacemakers, pacemaker electrodes, mechanical heart valves, endocardial leads, artificial heart valves, cardiac assistance devices, implantable cardiac stimulation devices, implantable pacemaker cardioverter defibrillator (ICD), cardiac rhythm management device, coronary shunts, cerebrospinal fluid shunts, dialysis machines, catheters, dialysis catheters, prosthesis, vascular implants, aortic implants, tissue implants, cardiovascular implants, drug delivery devices, medical delivery pumps, effectors, hemostasis valves, annuloplasty devices such as bands or rings, which are placed around the annulus of the mitral valve to decrease the risk of annular dilation and tension of the suture.

The non-living medical device may comprise a first component such as a matrix or non-biological material, including carbon, carbon polymers, inorganic fibers, nanofibers, amorphous carbon, pyrolytic carbon, vitreous carbon and glassy carbon), wood, cellulose, fibrin, elastin, porcine, human biological members e.g., cellular material, tissue, organ and proteins, metals e.g., platinum, iridium, tantalum, and titanium, alloys, aluminum oxide, silicone elastomer, rubber, polymer, polylysine, polyglycolic acid, polyamide, polyolefin, polyester, poly-paradioxane, polycarbonate, polyether, polyvinyl chloride, polyurethane, polystyrene, polyacrylate polyethylene, polypropylene, polytetrafluoroethylene or a combination thereof. A cloned biological material (i.e., shaped tissue structure or shaped organ structure) may be attached to a second component on the non-living medical device. The first component and the second component may be operatively attached for providing treatment, diagnosis, cure, mitigation and prevention of disease, injury, handicap or condition in a living organism.

The cloned biological materials (i.e., shaped tissue structures or shaped organ structures) may be used on a non-living medical devices comprising a first component such as a matrix or non-biological material of alloys including, but are not limited to titanium alloys, iridium alloys, magnesium alloys, copper alloys, platinum alloys, molybdenium alloys, stainless steel, (e.g. 316L), nickel alloys, nickel-titanium alloys, tantalum alloys, cobalt-iron alloys, chromium cobalt alloys (e.g. Elgiloy), chromium cobalt-nickel alloys, chromium cobalt-nickel molybdenium alloys. The cloned biological materials (i.e., shaped tissue structures or shaped organ structures) may be used on non-living medical devices comprising a first component of platinum alloys including, but are not limited to platinum-iridium. The cloned biological materials (i.e., shaped tissue structures or shaped organ structures) may be used on a non-living medical device comprising a first component of chromium cobalt-nickel molybdenium alloys including, but are not limited to MP3 5N, which is the trademark for a chromium cobalt-nickel molybdenium alloy, consisting of 35% cobalt, 35% nickel, 20% chromium and 10% molybdenium and MP20N, which is the trademark for a chromium cobalt-nickel molybdenium alloy, consisting of 50% cobalt, 20% nickel, 20% chromium and 10% molybdenium.

Figure 6:
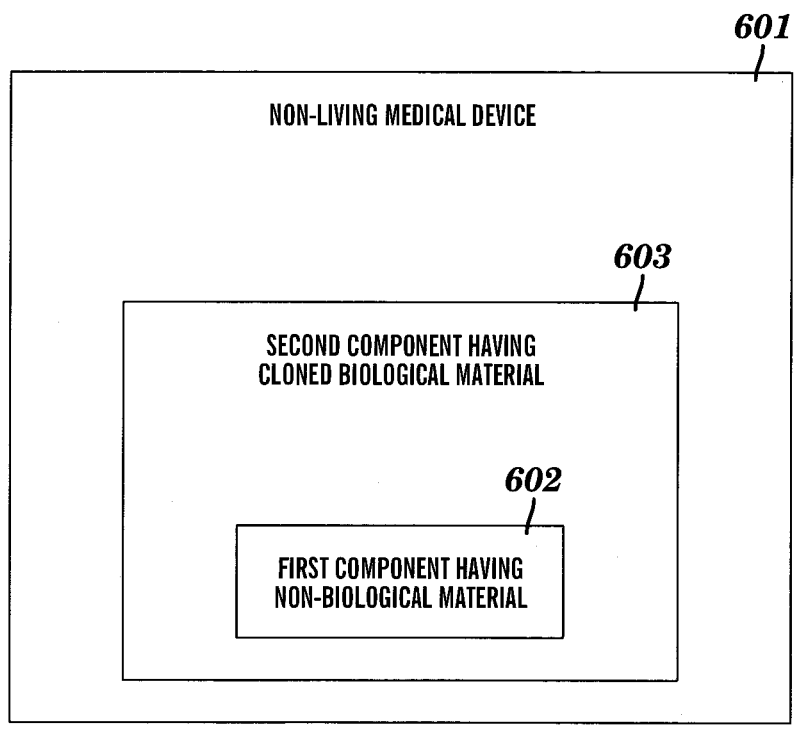
FIG. 6 illustrates a medical device comprising a first component having non-biological material and second component having cloned biological material attached and operatively associated in a non-living medical device for treatment, diagnosis, cure, mitigation and prevention of disease, injury, handicap or condition in a living organism.

FIG. 6 illustrates a medical device comprising a first component having non-biological material and second component having cloned biological material attached and operatively associated in a non-living medical device for treatment, diagnosis, cure, mitigation and prevention of disease, injury, handicap or condition in a living organism.

Figure 7:
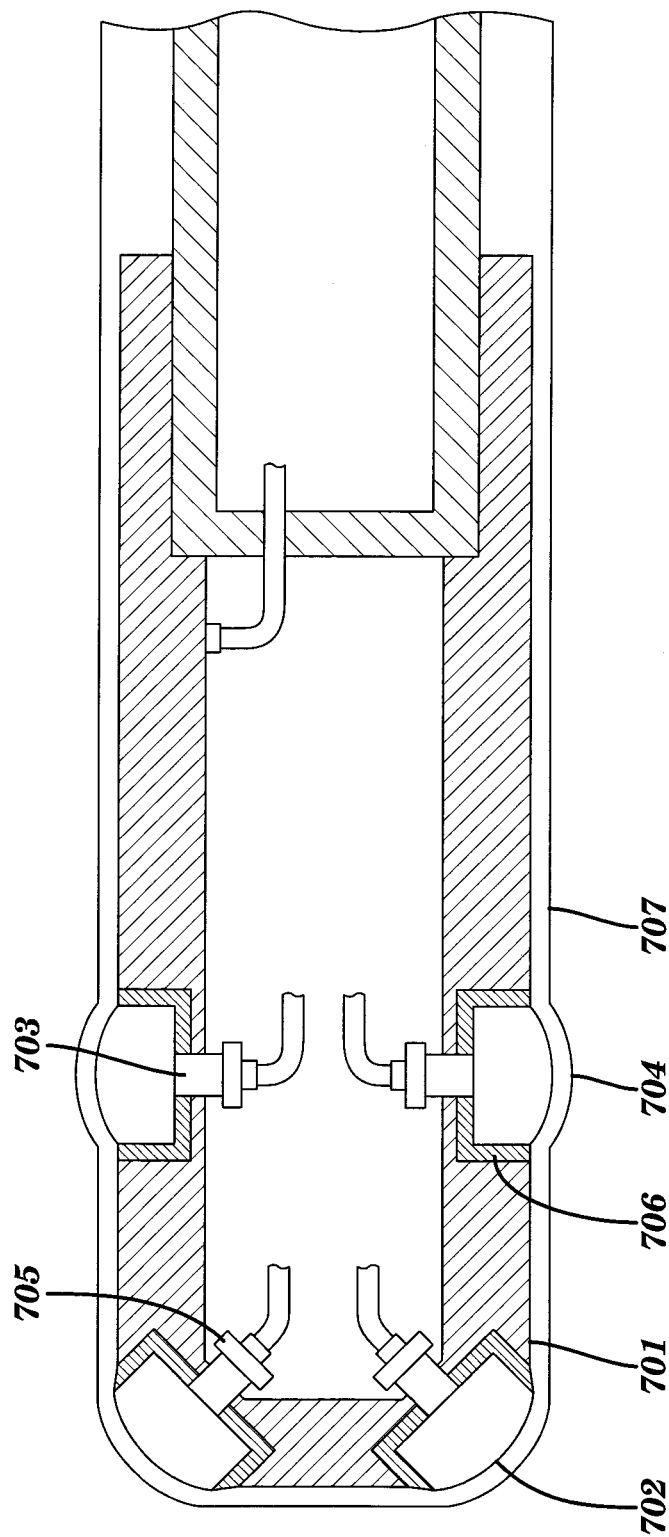
FIG. 7 illustrates a cloned biological material such a shaped tissue structure grown from cloned cells for use as an enclosure on a catheter for preventing immunological reaction.

A cloned biological material (a shaped tissue structure or a shaped organ structure) may be used on a non-living medical device or as part of a non-living medical device (i.e., tube, bolt, screw, and gasket). In one aspect of the present invention, the cloned biological material (i.e., shaped tissue structure or shaped organ structure) is a second component grown from cloned cells may be used as an enclosure (i.e., covering or casing) on a catheter for preventing or reducing immunological reactions when the catheter is inserted into a patient. FIG. 7 illustrates a cloned biological material such as a shaped tissue structure is a second component grown from cloned cells used as an enclosure of a catheter for preventing immunological reaction. FIG. 7 shows a catheter, including a distal cap 701, mapping electrodes 702, 704, a base stem 703, insulating sleeve 706 and base electrode 705. In FIG. 7, the shaped tissue structure enclosure 707 surrounds the distal cap 701 of the catheter, the mapping electrode 702, 704, base electrode 705 and insulating sleeve 706.

Figure 8:
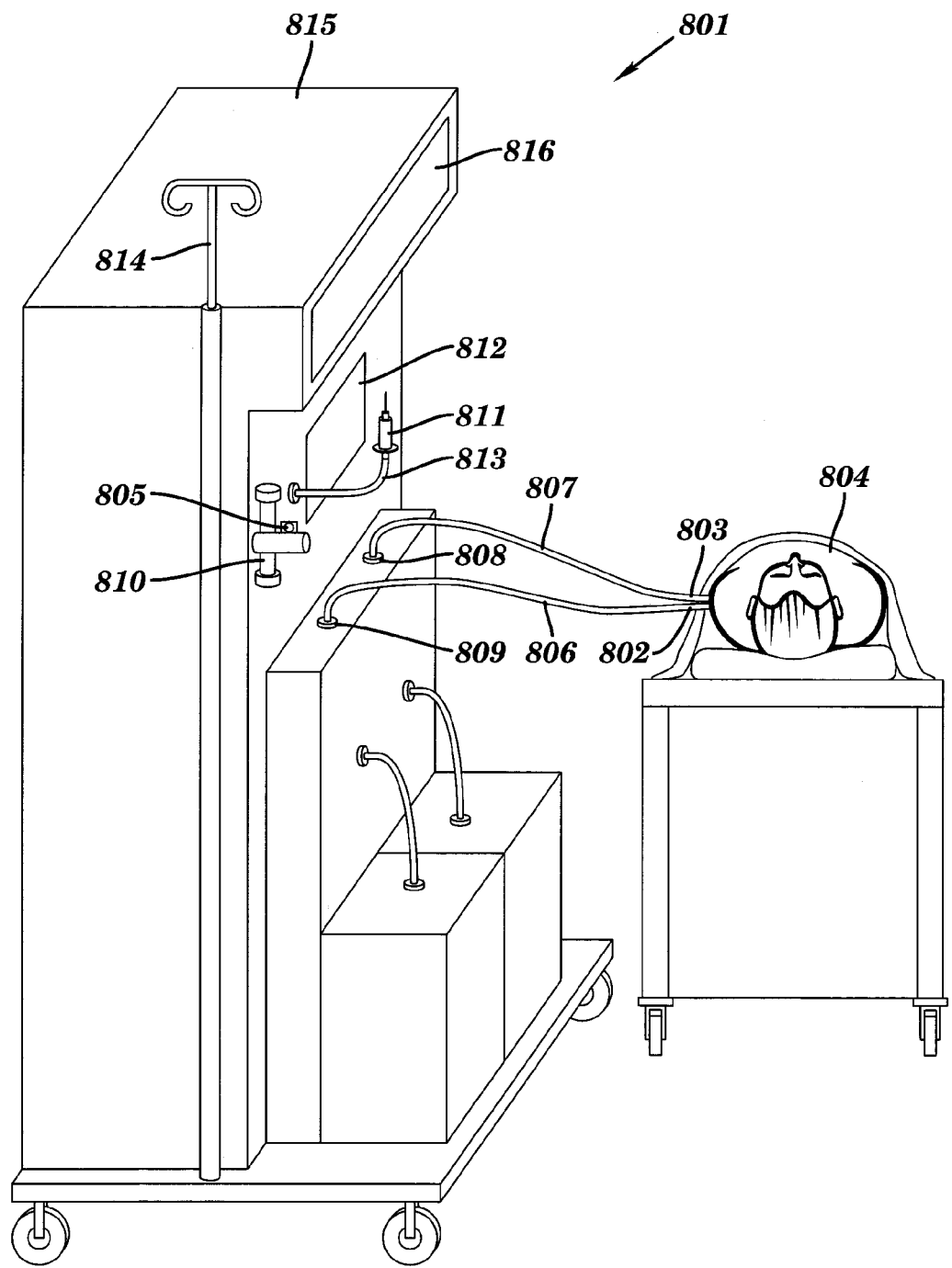
FIG. 8 and FIG. 8A show simplified examples of cloned biological material such as shaped tissue structures or shaped organ structures in the form of a dialysis venous tube and a dialysis arterial tube for a dialysis medical machine.
Figure 8A:
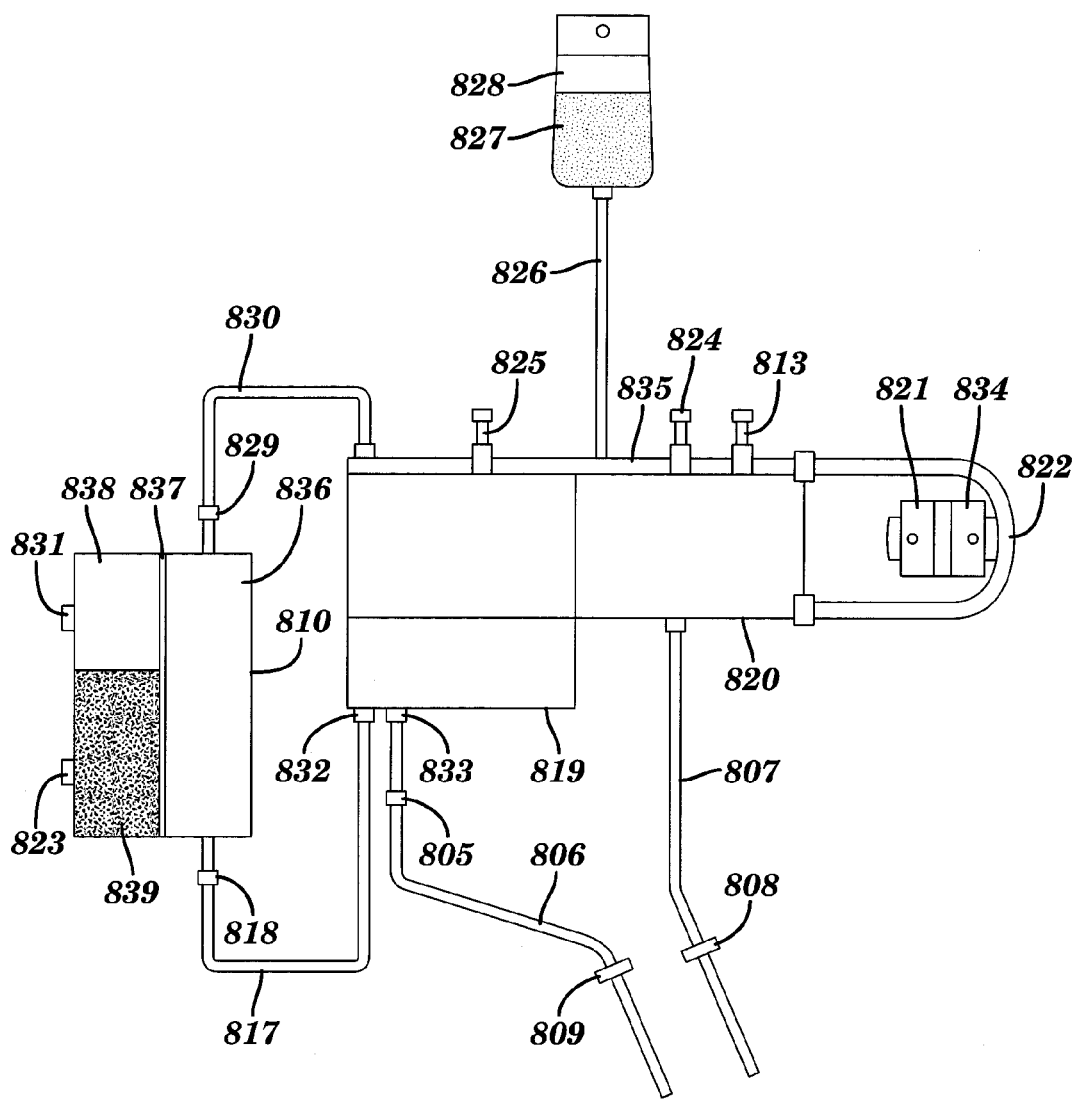
Figure 8B:
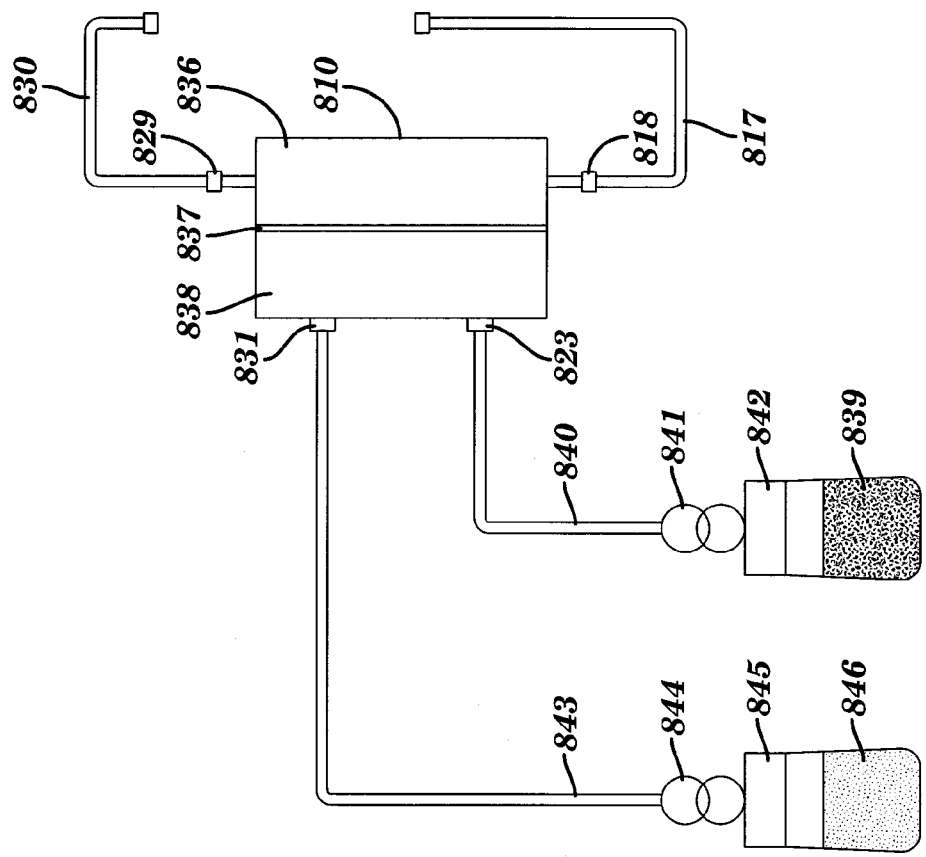
FIG. 8B illustrates an examples of cloned biological material such as shaped tissue structures or shaped organ structures in the form of connector tubes of a dialysis medical machine.

A cloned biological material (i.e., a shaped tissue structure or a shaped organ structure) may be used as a dialysis catheter enclosure for a nonliving medical device such as a dialysis medical machine or a part (i.e., a dialysis tube) on a dialysis medical machine (i.e., kidney dialysis machine). In accordance with FIG. 8, cloned biological material (i.e., shaped tissue structures or shaped organ structures) may be as a second component in the form of tube on a non-living medical device such as a dialysis medical machine. FIG. 8 and FIG. 8A show simplified examples of cloned biological materials (i.e., shaped tissue structures or shaped organ structures) as a second component in the form of a dialysis venous tube 806 and cloned biological materials in the form of a dialysis arterial tube 807 for a dialysis medical machine 801, FIG. 8B illustrates examples of cloned biological materials (i.e., shaped tissue structures or shaped organ structures in the form of connector tubes of a dialysis medical machine.

In accordance with FIG. 8 and FIG. 8A, the dialysis medical machine 801 may include a rotator 821, a pump 834 and a pump head 822 for pumping blood from a dialysis patient 804 through a dialysis arterial tube 807 to an arterial cavity 820 and pumping blood from an arterial cavity 820 to chamber 835. The dialysis arterial tube 807 receives blood from a dialysis patient and transports blood to an arterial cavity 820. The arterial cavity 820 receives blood through the dialysis arterial tube 807. An arterial tubing fastener 808 prevents the flow of blood from the dialysis patient through the dialysis arterial tube 807 to the arterial cavity 820.

A dialysis sterilizer 810 sterilizes blood that is transported to the dialysis sterilizer 810. A cloned biological material (i.e., a shaped tissue structure or shaped organ structure) as a second component in the form of first connector tube 830 transports blood through a blood port 829 of the dialysis sterilizer 810. A first cavity 836 of the dialysis sterilizer 810 receives blood from the blood port 829. A dialysis solution pump 841 transports a dialysis solution 839 from a dialysis solution source 842 through a dialysis solution tube 840. The dialysis solution 839 is further pumped through a dialysis port 823 to a second cavity 838. A sterilizer filter 837 filters waste from the blood. The second cavity 838 receives the waste that will be added to the dialysis solution 839 in the second cavity 838. A blood duct 818 receives sterilized blood from the dialysis sterilizer 810. A cloned biological material (i.e., a shaped tissue structure or a shaped organ structure) in the form of second connector tube 817 transports sterilized blood from the blood duct 818 to a venous cavity 819.

The venous cavity 819 receives sterilized blood transported from the blood duct 818 via the second connector tube 817 to a venous port 832 of the venous cavity 819. A cloned biological material (i.e., a shaped tissue structure or shaped organ structure) in the form of venous cavity tube 825 receives the sterilized blood from the venous cavity 819. A bubble indicator 805 expels air in the sterilized blood. The sterilized blood leaves the venous cavity 819 through a venous duct 833. A venous tubing fastener 809 clamps the dialysis venous tube 806 and prevents the transport of air from the venous cavity 819 through the dialysis venous tube 806 when the bubble indicator 805 detects air in the sterilized blood. The dialysis venous tube 806 transports sterilized blood to the dialysis patient.

After the sterilizer filter 837 filters waste from the blood, the second cavity 838 receives the waste, and the waste is added to the dialysis solution 839 in the second cavity 838, the waste dialysis solution 846 of FIG. 8B is transported through waste duct 831 of the second cavity 838. A waste dialysis solution pump 844 is used to pump the waste dialysis solution 846 through a waste tube 843 into a waste container 845.

The dialysis medical machine 801 may also include a stand 814 for holding the saline bag 828. Saline 827 in a saline bag 828 may be transported through a saline tube 826 and may be used to return any remaining blood in the arterial cavity 820 to the dialysis patient. The dialysis medical machine 801 may include a syringe 811 and syringe tube for delivering heparin to the chamber 835 to reduce or preventing coagulation of the blood. The dialysis medical machine may also include a covering 812 and a covering 815. The dialysis medical machine 801 may include a touch sensitive screen 816 for inputting and outputting information.

Figure 9:
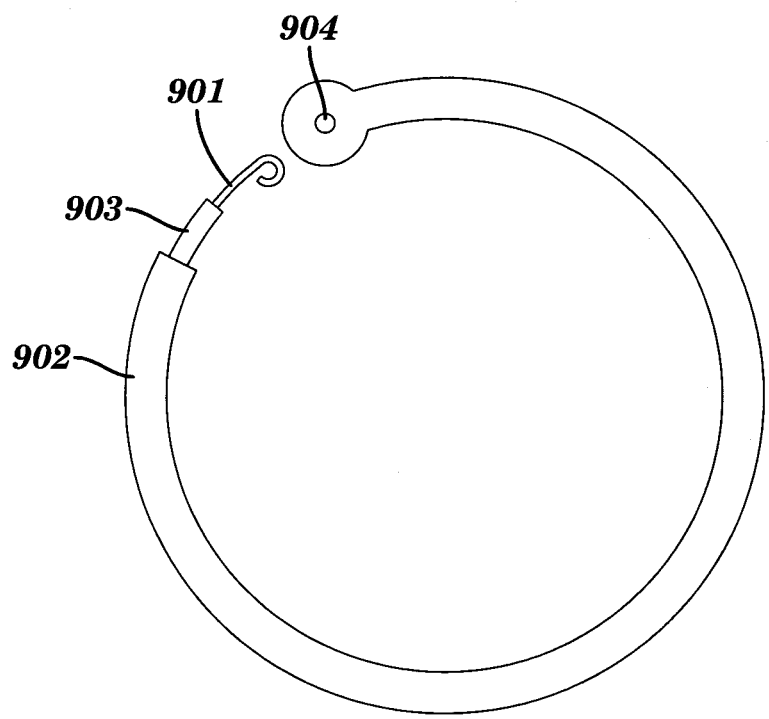
FIG. 9 illustrates a cloned biological material such as a shaped tissue structure grown from cloned cells used as tubing on an annuloplasty band for preventing immunological reaction.

FIG. 9 illustrates a cloned biological material (i.e., a shaped tissue structure) grown from cloned cells used as a second component (i.e., a tube) on an annuloplasty band for preventing the deleterious effects from bodily contact with foreign or artificial material of the annuloplasty band. FIG. 9 shows wires 901, a sheath 902, tube 903 and a suture 904 of an annuloplasty band. Wires 901 of an annuloplasty band may be comprised of copper. The wires may be insulated by a sheath 902 and/or tube 903. The tube 903 may be comprised of a shaped tissue structure, derived from cloned cellular material that is compatible with the patient receiving the annuloplasty band.

Figure 10:
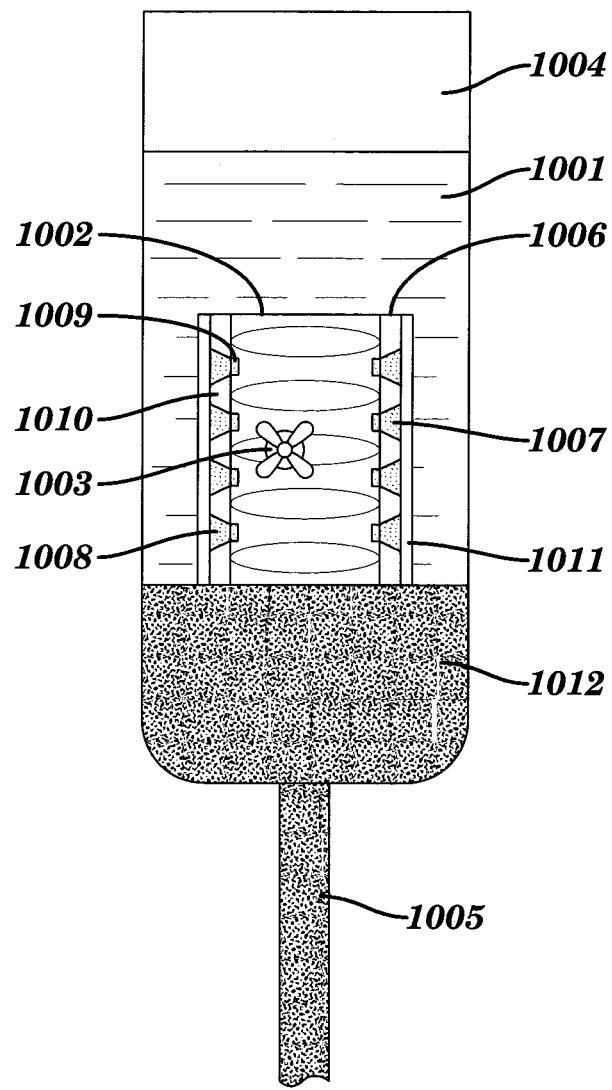
FIG. 10 illustrates cloned biological material such as a shaped tissue structure grown from cloned cells as drug delivery tube on a drug delivery device for preventing immunological reactions.
Figure 10A:
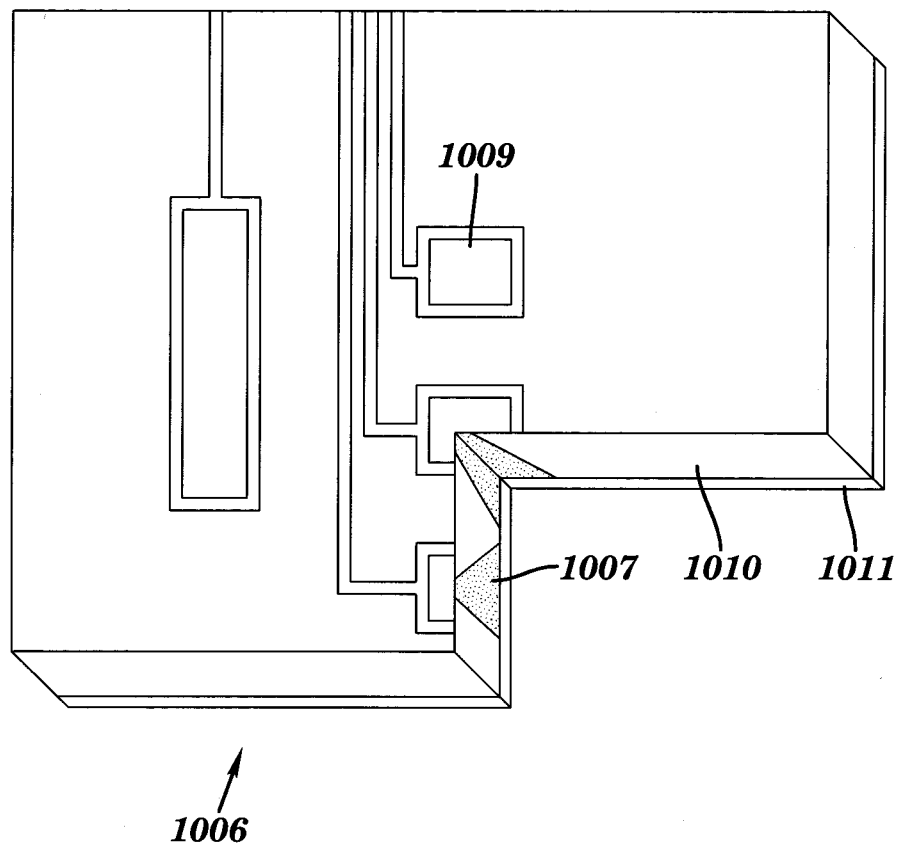
FIG. 10A illustrates a simplified example of a dialysis microchip device.

A cloned biological material (i.e., a shaped tissue structure or a shaped organ structure) may be used as a part (i.e., a tube) on a non-living medical device such as a drug delivery device. FIG. 10 illustrates an example of a cloned biological material (i.e., a shaped tissue structure) from cloned cells used as a drug delivery tube for a drug delivery device for providing treatment, diagnosis, cure, mitigation and prevention of diseases, injury handicap or condition in a living organism. FIG. 10 shows an intravenous container 1004 and a microchip device 1006. A substrate 1010 may have at least one a reservoir 1007. A seal 1011 seals base of the reservoir 1007. A reservoir 1007 contains drug molecules 1008 for release. A reservoir top 1009 covers the reservoir 1007 containing the drug molecules 1008. The reservoir top 1009 is selectively permeable to the drug molecules 1008 in the reservoir 1007. Thus, the drug molecules 1008 may be released from the reservoir top 1009 of the reservoir 1007 and mixed with a fluid 1001 of a chamber 1002. The fluid 1001 of the chamber 1002 may be further mixed with drugs molecules 1008 using a mixer 1003. The mixture 1012 of fluid 1001 and drug molecules 1008 passes through the intravenous container 1004. Then, the mixture 1012 flows through a drug delivery tube 1005 intravenously to a patient. FIG. 10A illustrates a simplified example of a microchip device 1006, including a substrate 1010, a reservoir 1007, drug molecules 1008 for release, a reservoir top 1009 and a seal 1011.

Figure 11:
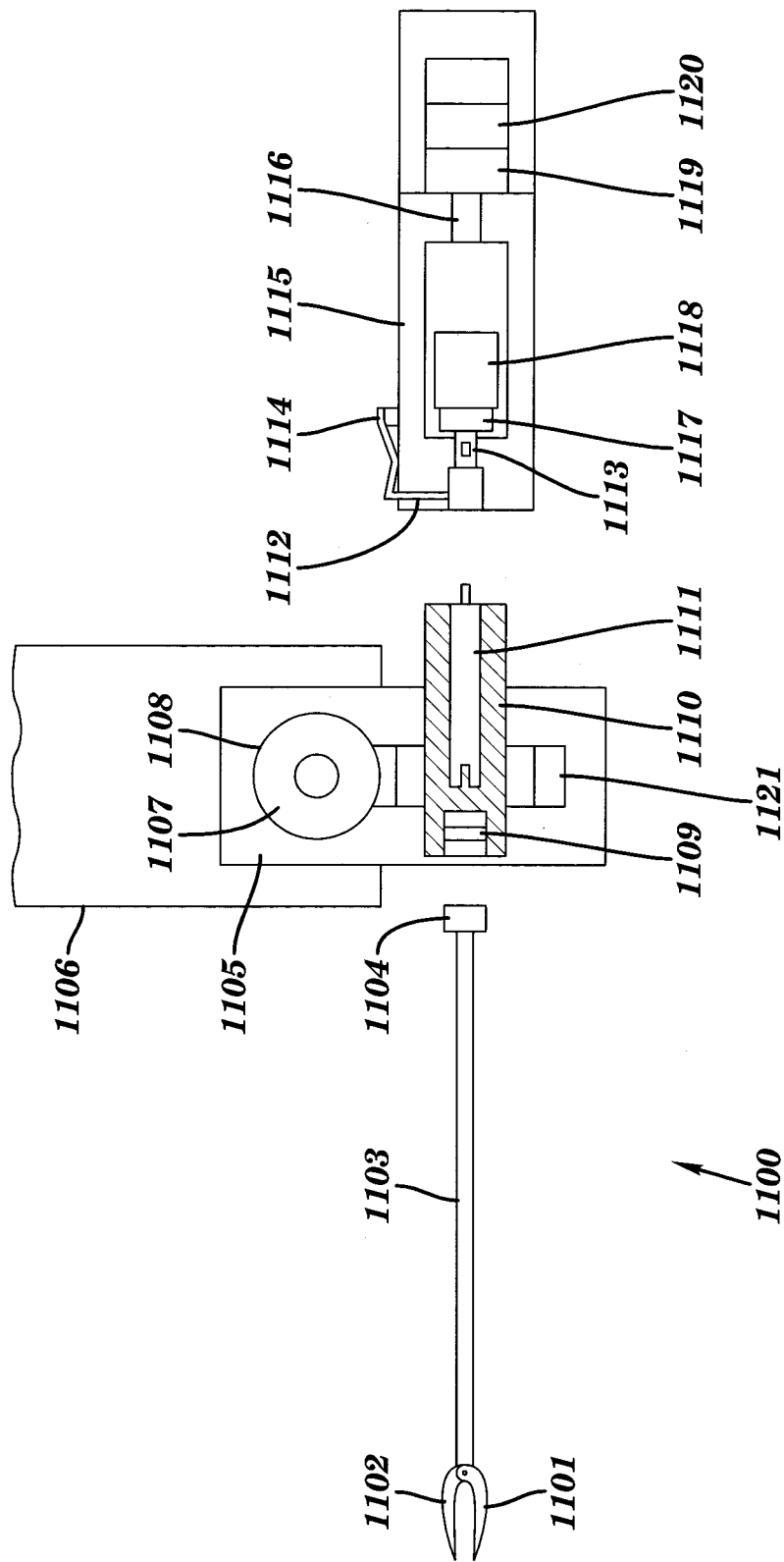
FIG. 11 illustrates a cloned biological material such as a shaped tissue or organ structure in the form of a screw in an end effector of a robotic surgical arm.

FIG. 11 illustrates a cloned biological material (i.e. a shaped tissue or organ structure) in the form of a screw 1116 in a non-living medical device such as an end effector 1100 of a robotic surgical arm 1106. The end effector 1100 may include a surgical device 1103, comprising finger 1101, finger 1102, a surgical rod 1103 and a surgical sleeve 1104. The surgical device 1103 may be connected to a driver 1115. The driver 1115 includes a cylinder 1113 and a driver cell 1117. A transmission gear enclosure 1119 is connected to a reverse gear motor 1120. The driver 1115 may be attached to a nut 1118. The nut 1118 may be attached to a cloned biological material (i.e., a shaped tissue structure or a shaped organ structure) as a second component formed into a screw 1116. The end effector 1100 may be mounted on a robotic surgical arm 1106 using a connector assembly 1108, including a collar 1121, a holder 1110 and a motor gear device 1107. The holder 1110 includes a shaft 905. The motor gear device 1107 is powered by a motor in the connector assembly 1108 of the robotic surgical arm 1106. The motor gear device 1107 causes the collar 1121 to rotate. In turn, the surgical device 1103 rotates. A pin 1112 may be received by an aperture 1111 of the driver 1115. When the aperture 1111 of the driver 1115 receives the pin 1112, the decoupling device 1109 is secured to the driver 1115. The decoupling device 1109 may be used to disconnect the surgical device 1103 from the driver 1115.

Figure 12:
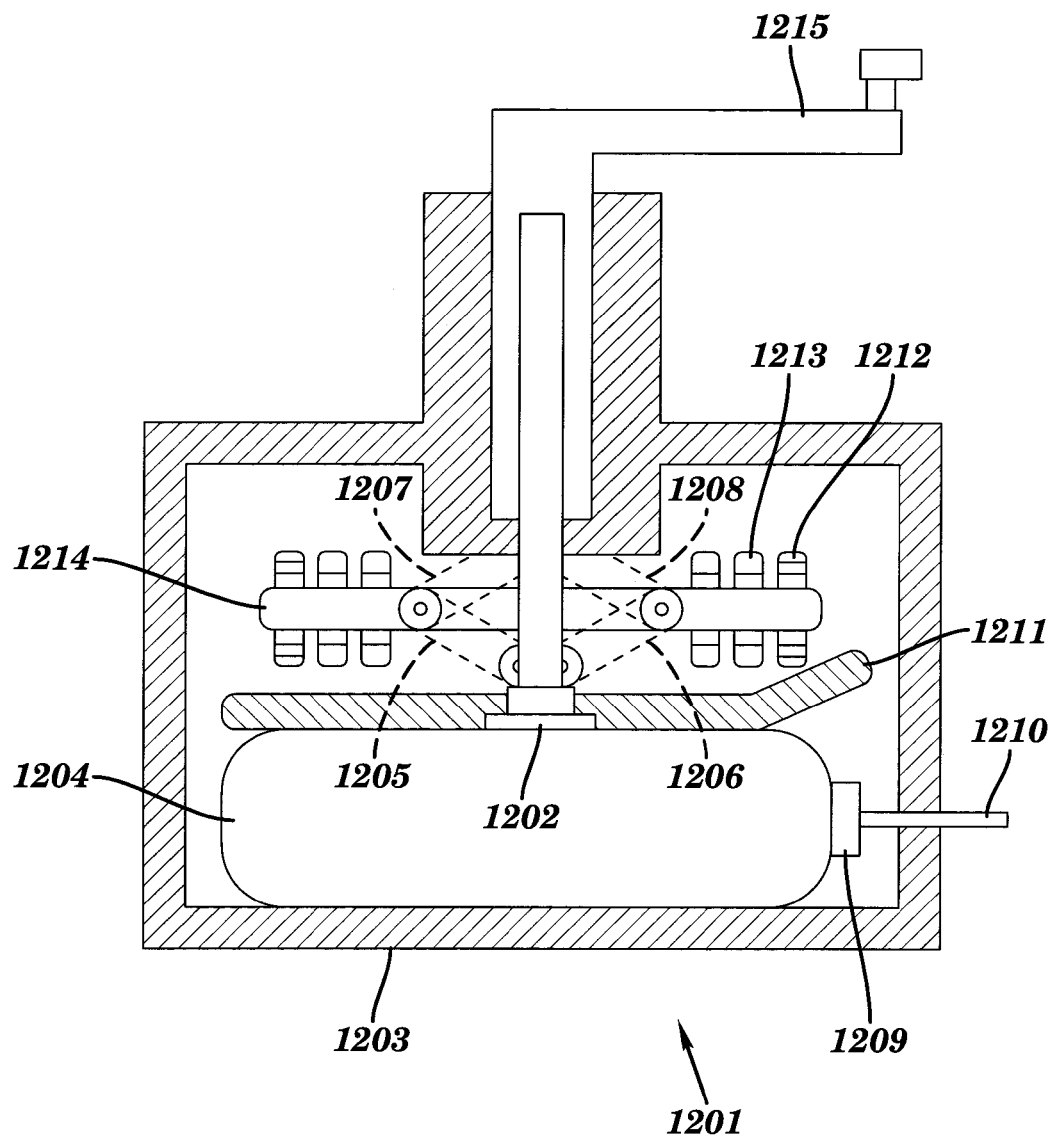
FIG. 12 and FIG. 12A illustrate examples of a cloned biological material such as a shaped tissue structure or organ structure grown from cloned cells in the form of a bolt on a medical device or medical machine such as an medical delivery pump for delivering drugs to a patient.
Figure 12A:
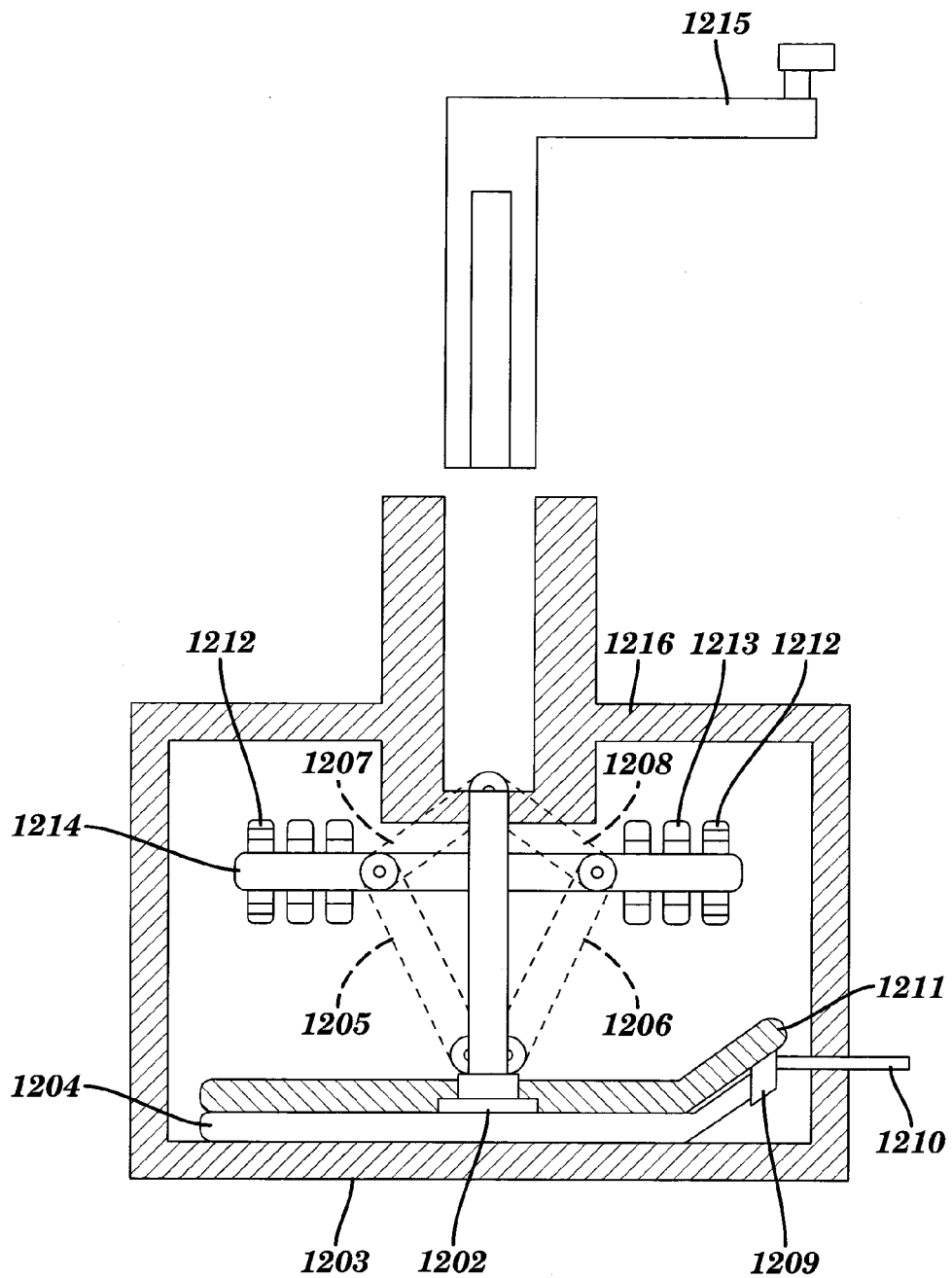

FIG. 12 and FIG. 12A illustrate examples of a cloned biological material (i.e., a shaped tissue structure or a organ structure) grown from cloned cells in the form of a bolt on a non-living medical device or medical machine such as an medical delivery pump for delivering drugs to a patient. The cloned biological material in the form of a bolt may be second component of the nonliving medical device. In FIG. 12 illustrates an example of an medical delivery pump 1201, including a bolt 1202, comprised of a cloned biological material (i.e., a shaped tissue structure or organ structure) grown from cloned cells. The medical delivery pump 1201 may include a bottom support covering 1203, a receptacle 1204, arms 1205, 1206, 1207 and 1208, fluid vessel 1209, line 1210, plate 1211, slide 1212, spring 1213, guide 1214 and handle 1215, top support covering 1216. FIG. 12A illustrates a medical delivery pump 1201 with a depressed receptacle 1204. The receptacle 1204 may be depressed as the handle 1215 is turned to disengage the handle 1215 from the bolt 1202 causing the plate 1211 to descend toward the bottom support covering 1203.

Figure 13:
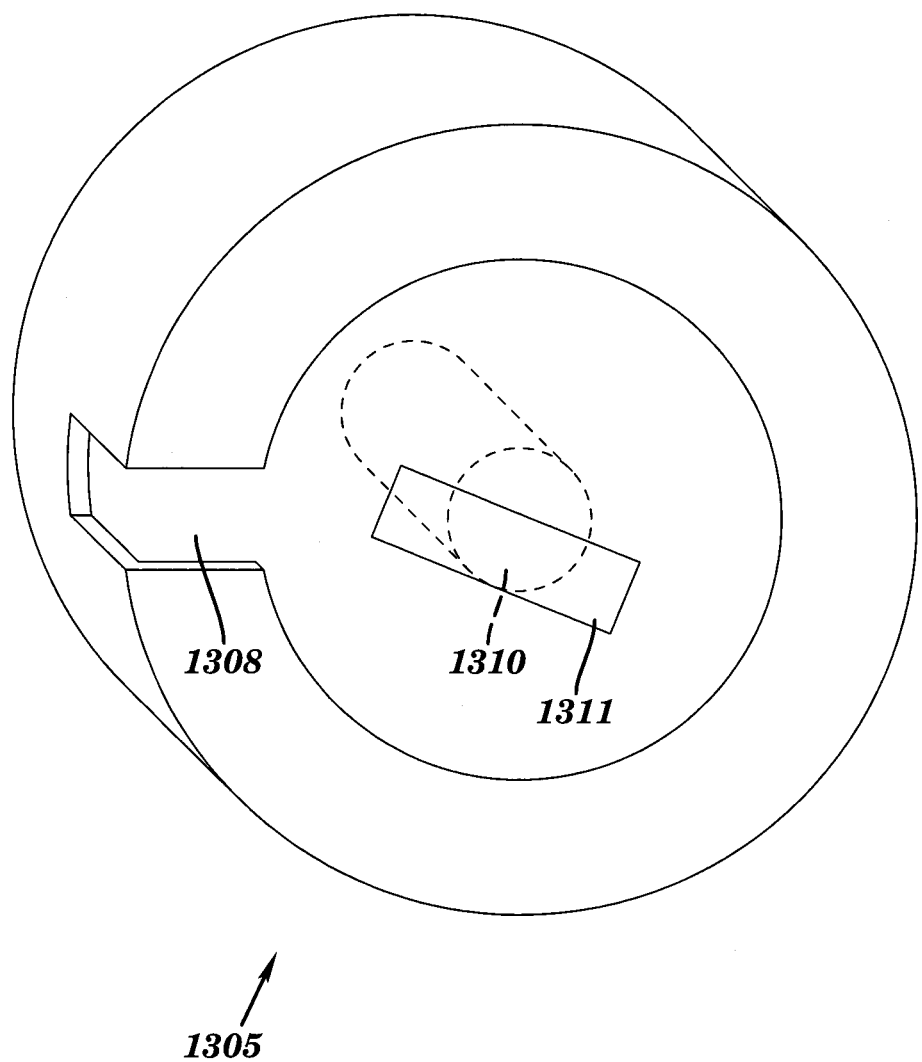
FIG. 13 and FIG. 13A illustrate examples of a cloned biological material such as a shaped tissue structure or a shaped organ structure in the form of a gasket for a hemostatic valve.
Figure 13A:
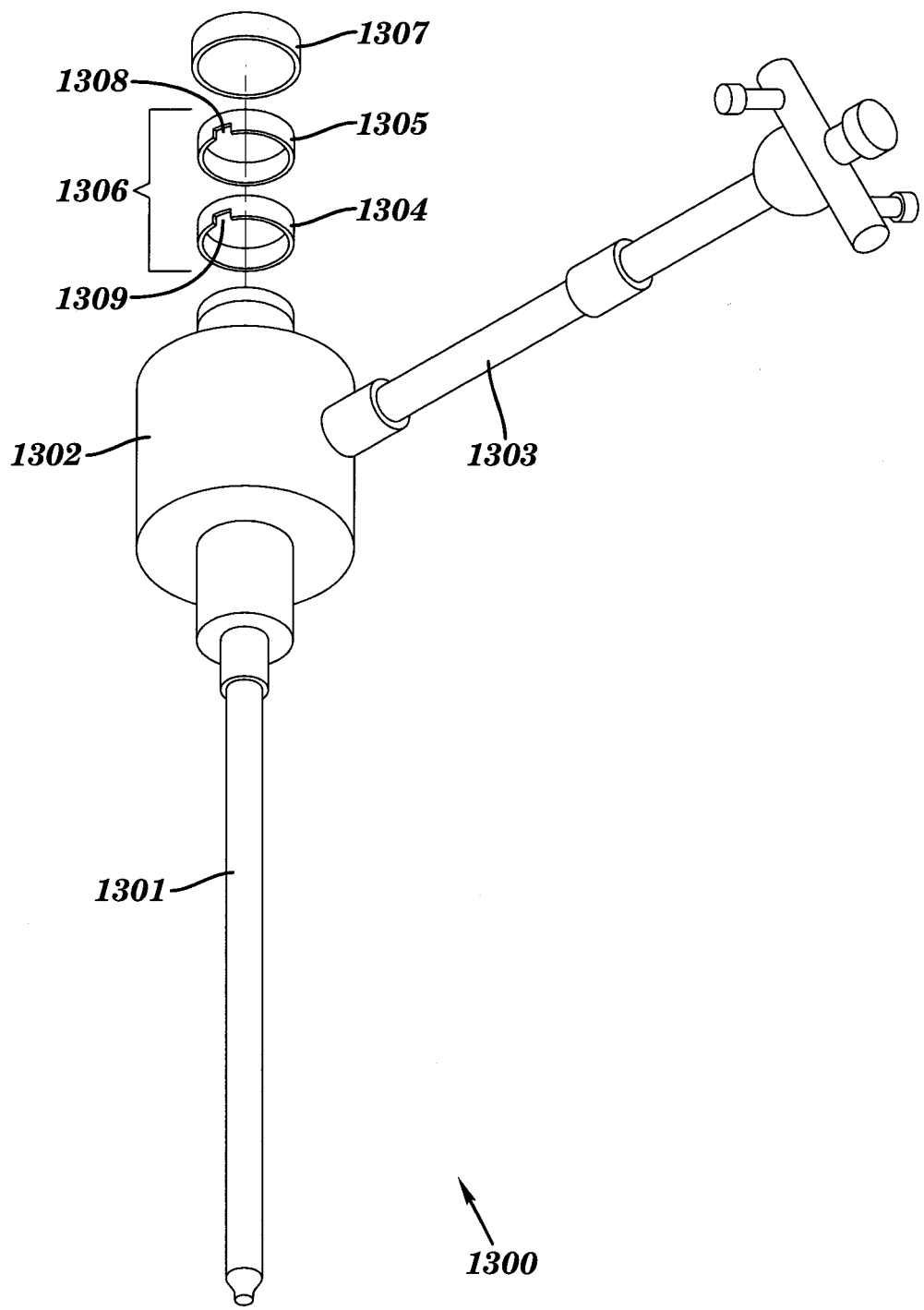

FIG. 13 illustrates an example of a cloned biological material (i.e., a shaped tissue structure or a shaped organ structure) as a second component in the form of a gasket 1305. FIG. 13A shows a hemostasis assembly 1300 comprising a sheath 1301, a housing 1302, a hemostasis port 1303, a hemostasis valve 1306 and a hemostasis top 1307. The sheath 1301 may be a tubular shaped tissue or tubular organ structure formed from cloned biological material. The hemostasis valve 1306 may include a gasket enclosure 1304 and a cloned biological material (i.e. shaped tissue or organ structure) in the form of a gasket 1305. The gasket 1306 may include an aperture 1310 and slit 1311 for receiving a catheter. The projecting part 1309 of the gasket enclosure 1304 may be slid over the notch 1308 of the gasket 1305 to secure the gasket enclosure 1304 to the gasket 1305. The hemostasis valve 1306 may be positioned inside the housing 1302. The hemostasis top 1307 may be attached, adhered, fused, compressed or threaded to the housing 1302.

Figure 14:
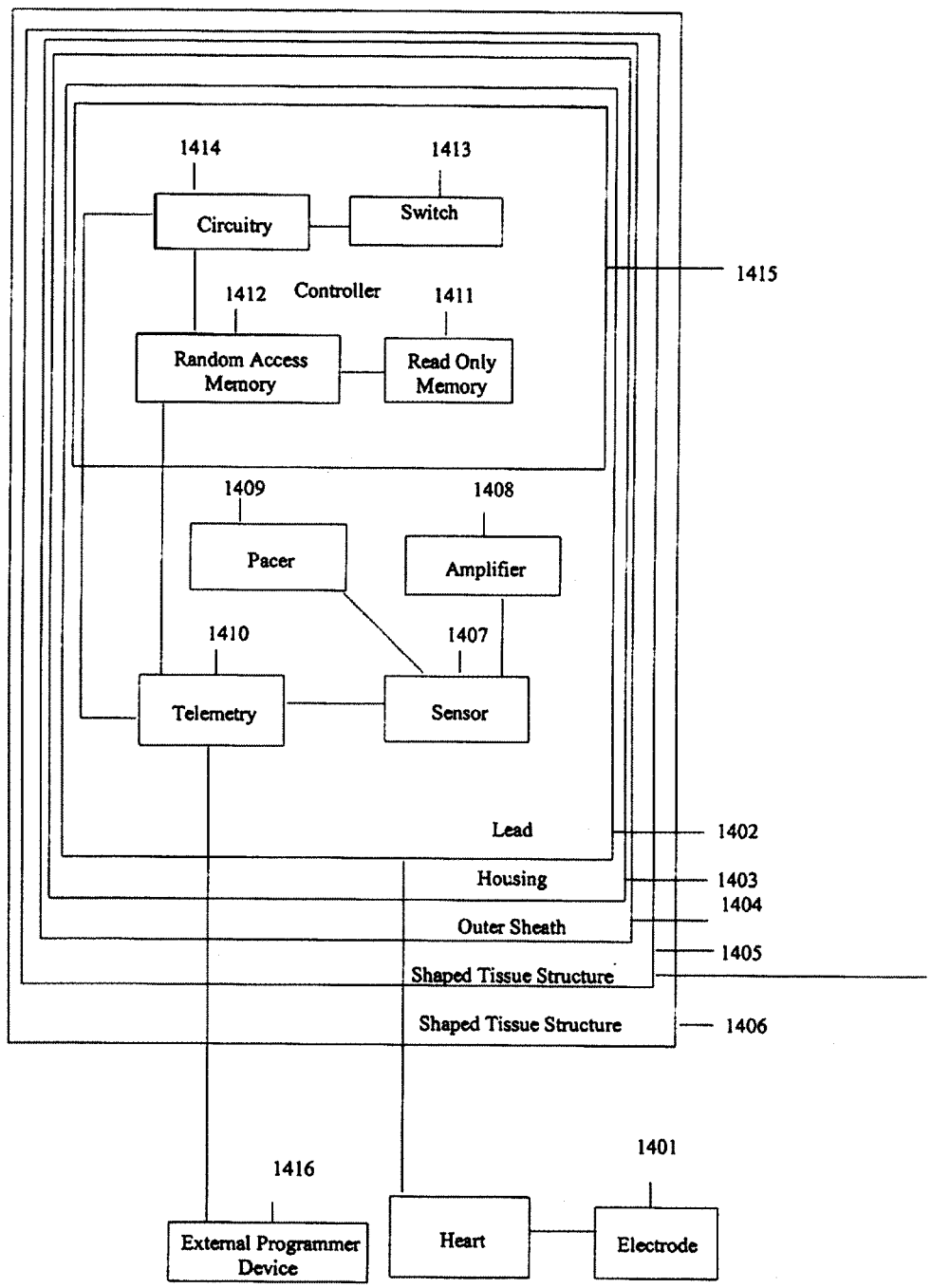
FIG. 14 illustrates a cloned biological material such as a shaped tissue structure grown from cloned cells for use on a pacemaker for treatment, diagnosis, cure, mitigation and prevention of disease, injury, handicap or condition in a living organism.

In another aspect, the present invention provides a cloned biological material (i.e., a shaped tissue structure or a shaped organ structure) grown from cloned cells for use on a cardiac assist device for creating or improving medical machines or non-living medical devices and preventing immunological reactions such as compliment activation. FIG. 14 illustrates a cloned biological material such as a shaped tissue structure grown from cloned cells for use on a pacemaker for treatment, diagnosis, cure, mitigation and prevention of disease, injury, handicap or condition in a living organism. A non-living medical device may include a cardiac assist device. A cardiac assist device such as a pacemaker determines whether the heart is beating at an abnormal cardiac rhythm. The pacemaker responds by returning the heart to the normal cardiac rhythm. The pacemaker provides electrical stimulation to the atrium or ventricle of the heart by delivering pacing pulses to the chamber of the heart. Alternatively, the pacemaker may provide dual heart chamber electrical stimulation to the atrium and ventricle.

The pacemaker is subcutaneously implanted into the heart. The pacemaker includes one or more leads 1402 (i.e., unipolar lead, bipolar lead), extending from the pacemaker, for implantation into the heart. The leads 1402 may include a right ventricular lead and/or an atrial lead. The pacemaker may include an amplifier 1408 for determining whether a signal exceeds a specified threshold. The lead 1402 stimulates electrical pacing pulses and senses electrical signals from the at particular sites. For example, the pacemaker may be connected to the patient via the right ventricular lead. The right ventricular lead monitors the conditions and indicators of the right ventricular and stimulates electrical pulses to the right ventricular.

The leads 1402 comprise electrodes, positioned close to the chamber of the heart. The electrodes 801 may be one of a ring electrode, a tip electrode, coil electrode and/or combination thereof. The electrodes 1401 of the lead sense the rhythmical cardiac activity, physiological conditions and electrical cardiac functions.

Each electrode 1401 (i.e., ring electrode, a tip electrode, coil electrode) is connected to the circuitry 1414 (i.e., electrical conductor), which is located within the lead body. A connector block receives a connector, which may be located at the proximal end of the ventricular lead. The connector block is attached to a housing.

The lead comprises a lead body. Within the lead body is the circuitry 1414 of the pacemaker. A housing 1403 (i.e., metal encasing, hermetically sealed enclosure, case) holds a controller 1415 therein. The housing 1403 may be encased within an outer sheath 1404 that electrically insulates the circuitry 1414 of the housing. Alternatively, the outer sheath 1404 may encase the housing 1403 and lead 1402. Further, a cloned biological material (i.e., a shaped tissue structure) 1406, surround the outer sheath 1404 of the pacemaker to protect the body from immunological reactions to the outer sheath 1404 and prevent the compliment activation of blood such as the creation of microemboli that may occur from contact with outer sheath 1404 of the pacemaker. The cloned biological material (i.e., shaped tissue structure) 1406 may be grown from cloned cells.

The memory of the controller 1415 includes a read-only memory (ROM) 1411 and random-access memory (RAM) 1412. The controller (i.e., microprocessor) is linked to the memory through a bus. The read-only memory (ROM) 1411 of the controller 1415 stores programs for operation of the controller 1415. The controller 1415 may be programmed through an external programming device 1416, which is not located in the housing 1403 of the pacemaker. The random-access memory (RAM) 1412 stores data such as measurements of impedance. The controller 1415 processes digital signals. The controller 1415 stores the digital signals in the random access memory (RAM) 1412. The controller 1415 also controls the delivery of pacing pulses. The housing 1403 of the pacemaker may include a switch 1413 for operating the controller 1415. When a lead 1402 senses that the heart beat rate of a bradycardia patient is below the lower rate limit (LRL), electrical pacing pulses are delivered to the bradycardia patient. The controller 1415 may be interfaced with a telemetry system 1410 for communicating telemetry to a programmer. The programmer includes a display device, printer output device and/or combination thereof.

The present invention provides for creating or improving medical machines or non-living medical devices from the interfacing of at least two different materials selected from the group consisting of a shaped tissue structure, a shaped organ structure, a biological member. The circuitry of the non-living medical device is created from the electronic potential that results when different material are interfaced.

The method for reducing or preventing immune reactions and creating or improving medical machines or non-living medical devices, said method, further comprising: creating each and every part of said non-living medical device from at least one of a first group consisting of said shaped tissue structure, said shaped organ structure, and a combination thereof, and at least one of a second group consisting of a biological member and a combination thereof.

The biological member includes, but is not limited to an atom, a molecule, an enzyme, a protein, a cell, a bone, a tendon, a ligament, a vessel, a muscle, a joint, an artery, a vein, a nerve, a tissue and an organ.

Figure 15:
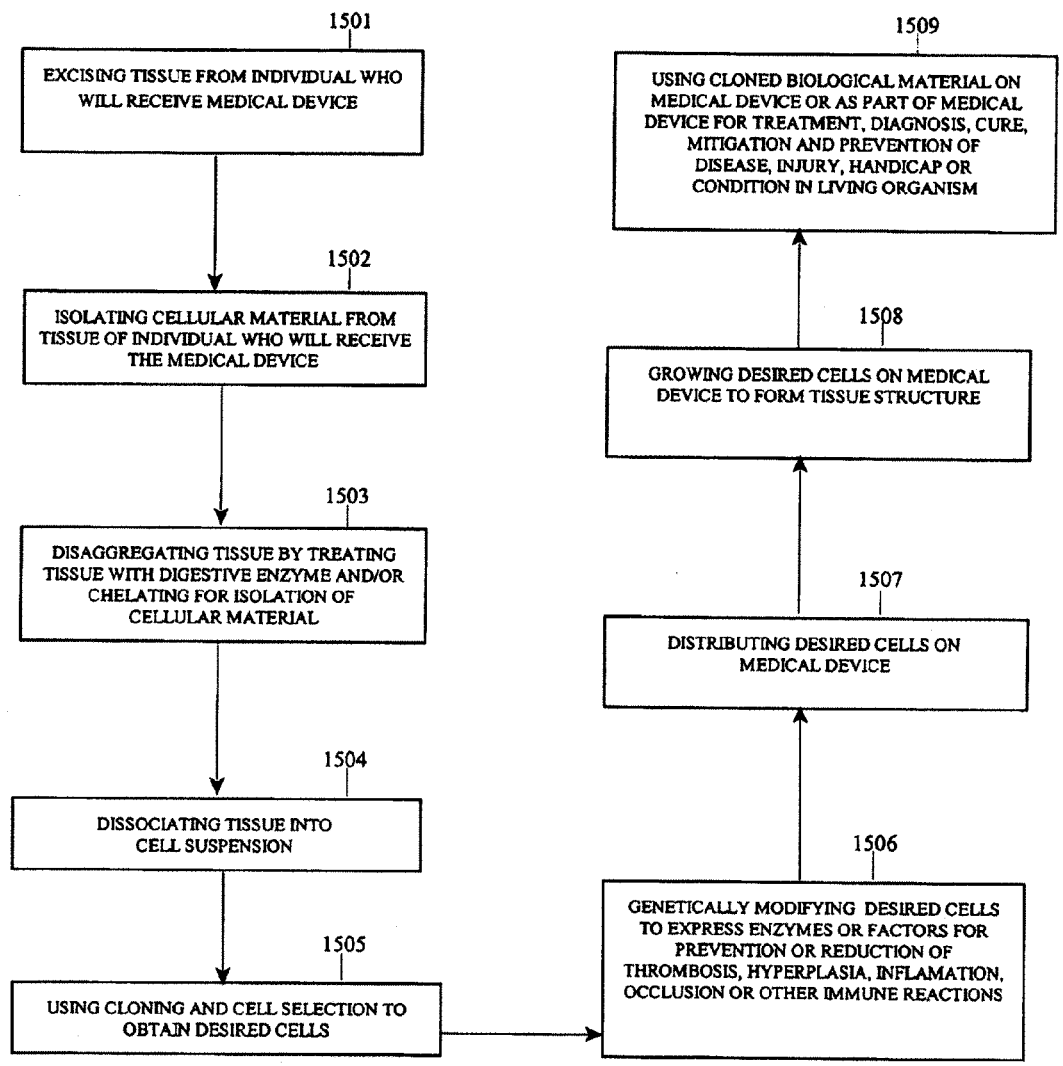
FIG. 15 illustrates a method of preparing a cloned biological material such as a shaped tissue structure or a shaped organ structure from a tissue or an organ including growing the desired cells on said medical device to form the shape of the cloned biological material.

In another aspect, the method of preparing a shaped tissue structure or a shaped organ structure from a tissue or an organ includes removing a portion of a tissue or an organ from an individual; isolating a cellular material from the portion of the tissue or the organ; dissociating the cellular material into a cell suspension using cell separation to obtain desired cells, and growing the desired cells on said non-living medical device to form the cloned biological material (i.e., shaped tissue structure or the shaped organ structure). FIG. 15 illustrates a method of preparing a cloned biological material (i.e., shaped tissue structure or a shaped organ structure) from a tissue or an organ includes growing the desired cells on said non-living medical device to form the shape of a biological cloned material in step 1508.

What is claimed is:

1. A method for reducing or preventing immune reactions resulting from contact with a non-living medical device comprising:

preparing a cloned biological material from a tissue or an organ, the cloned biological material being at least one of a shaped tissue structure of desired cells and a shaped organ structure of desired cells, wherein preparing the cloned biological material includes removing a portion of the tissue or the organ from a living organism, further wherein removing the portion of the tissue or the organ from the living organism includes excising the portion of the tissue or said organ; and utilizing the cloned biological material as a part of the non-living medical device via physical attachment, wherein a shape of the cloned biological material is modified or refined for attachment to the non-living medical device;

wherein the non-living medical device is a cardiac assist device, the cardiac assist device comprising a housing, said housing having a controller, a plurality of leads for sensing and receiving signals, an electrode for stimulating electrical pacing pulses to a heart, an outer sheath surrounding said housing, and the cloned biological material attached thereto forms a part of the non-living medical device to reduce or prevent immune reactions in the living organism that result from contact between the non-living medical device and the living organism;

wherein a part of the non-living medical device that makes contact with the living organism is comprised of the cloned biological material.

2. The method of claim 1, wherein the step of preparing said cloned biological material from said tissue or said organ further comprises:

isolating a cellular material from said portion of said tissue or said organ;

dissociating said cellular material into a cell suspension using cell separation to obtain desired cells; and growing the desired cells on a shaped matrix to form said cloned biological material.

3. The method of claim 2, wherein isolating said cellular material from said portion of said tissue or said organ includes disaggregating said cellular material from said tissue with a digestive enzyme.

4. The method of claim 3, wherein the digestive enzyme is selected from a group consisting of:

trypsin, chymotrypsin, collagenase, elastase, hydraluronidase, DNase, pronase, and dispase.

5. The method of claim 2, wherein isolating said cellular material from said portion of said tissue or said organ includes treating said tissue or said organ with a chelating agent.

6. The method of claim 1, wherein said tissue is a connective tissue.

7. The method of claim 2, wherein said desired cells are selected from a group consisting of:

pericytes, adipoctyes, macrophages, monocytes, plasma cells, mast cells, and endothelial cells.

8. The method of claim 1, wherein said tissue is selected from a group consisting of:

articular cartilage, auricular cartilage, costal cartilage, elastic cartilage, fibrous cartilage, hyaline cartilage, meniscal cartilage, and yellow cartilage.

9. The method of claim 2, wherein said desired cells are articular chronodrocytes from articular cartilage.

10. The method of claim 1, wherein said tissue is fetal neonatal foreskin.

11. The method of claim 2, wherein said cell separation to obtain said desired cells is selected from the group consisting of: negative separation, filtration, centrifugation, electrophoresis, unit gravity separation, cloning and cell selection, or a combination thereof.

12. The method of claim 2, wherein said shaped matrix is least one of a tubular structure, a thread-like structure, a twisted rope structure, a flat structure, a sheet structure, a spherical structure, a rod structure, a cubical structure or a combination thereof.

13. The method of claim 1, wherein preparing said cloned biological material includes removing said portion of said tissue or said organ from a donor.

14. The method of claim 2, wherein said shaped matrix comprises is at least one of a porous material, a non-porous material, a biodegradable material, a non-biodegradable material biodegradable material, and a combination thereof.

15. The method of claim 14, wherein said biodegradable material is selected from the group consisting of: a polyglycolic acid, a collagen, a polyorthoester, a polycaprolactone, a collagen sponge, a woven collagen, a gelatin, a polylactic acid, a polyglycolic acid, and combination thereof.

16. The method of claim 14, wherein said non-biodegradable material is selected from a group consisting of:

a polyamide, a polyester, a polyesteramide, a polystrene, a fluorinated ethylene propylene, a polypropylene, a polyacrylate, polyvinyl, a polycarbonate, a polytetrafluoroethylene, a polyethylene, a polyethylene terapthalate, a silicone, a silicone rubber, a polysulfone, a thermanox, a polyurethane, a polyacrylics, a polyhydroxymethyacrylate, and a nitrocellulose.

17. The method of claim 1, wherein said non-living medical device is comprised of a non-biological material selected from a group consisting of:

a carbon polymer, an inorganic fiber, a nanofiber, an amorphous carbon, a pyrolytic carbon, a vitreous carbon, a glassy carbon, a metal, an alloy, a silicone elastomer, a rubber, a polymer, a polylysine, a polyglycolic acid, a polyamide, a polyolefin, a polyester, a polyparadioxane, a polycarbonate, a polyether, a polyvinyl chloride, a polyurethane, a polystyrene, a polyacrylate polyethylene, a polypropylene, and a polytetrafluoroethylene.

18. The method of claim 1, wherein the cloned biological material is an enclosure on a catheter.

19. The method of claim 1, wherein said cloned biological material is a tube, a gasket, bolt or screw of the non-living medical device.

* * * * *